(12) United States Patent
Alberati et al.

(10) Patent No.: US 8,263,584 B2
(45) Date of Patent: Sep. 11, 2012

(54) IMIDAZOPYRIDINES

(75) Inventors: Daniela Alberati, Zofingen (CH);
Ruben Alvarez Sanchez, Rosenau (FR);
Konrad Bleicher, Freiburg (DE);
Alexander Flohr, Loerrach (DE);
Katrin Groebke Zbinden, Liestal (CH);
Matthias Koerner, Grenzach-Wyhlen (DE); Bernd Kuhn, Reinach BL (CH);
Jens-Uwe Peters, Grenzach-Wyhlen (DE); Markus Rudolph, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/151,310

(22) Filed: Jun. 2, 2011

(65) Prior Publication Data

US 2011/0294779 A1 Dec. 1, 2011

Related U.S. Application Data

(62) Division of application No. 12/886,657, filed on Sep. 21, 2010, now Pat. No. 8,017,604.

(30) Foreign Application Priority Data

Sep. 24, 2009 (EP) .................................... 09171253

(51) Int. Cl.
*A61K 31/437* (2006.01)
*A61K 31/5377* (2006.01)
*A61K 31/4985* (2006.01)
*A61K 31/553* (2006.01)
*A61K 31/541* (2006.01)
*C07D 519/00* (2006.01)
*C07D 471/04* (2006.01)
*A61P 25/22* (2006.01)
*A61P 25/18* (2006.01)

(52) U.S. Cl. ................ 514/210.18; 514/300; 514/233.2; 514/249; 514/211.15; 514/253.04; 514/228.2; 514/232.5; 544/127; 544/350; 544/349; 544/362; 544/58.2; 544/80; 546/121

(58) Field of Classification Search ............ 514/210.18, 514/300, 233.2, 249, 211.15, 253.04, 228.2, 514/232.5; 544/127, 350, 349, 362, 58.2, 544/80; 546/121
See application file for complete search history.

(56) References Cited

U.S. PATENT DOCUMENTS 7,297,698 B2 11/2007 Taniguchi et al.

FOREIGN PATENT DOCUMENTS

| EP | 1570847 | | 9/2005 |
|---|---|---|---|
| WO | WO2005/012485 | | 2/2005 |
| WO | WO2007/082806 | | 8/2007 |
| WO | WO2007/098169 | | 8/2007 |
| WO | 2008/113469 | * | 9/2008 |
| WO | WO2009/112679 | | 9/2009 |

OTHER PUBLICATIONS

Sano et al., "J. Neurochem." 105:546-556 ( 2008).
Coskran et al., "J. Histochem. Cytochem." 54(11):1205-1213 ( 2006).
Fujishige et al., "Eur. J. Biochem." 266(3):1118-1127 ( 1999).
Vandenberg et al., "Expert Opinion on Therapeutic Targets" 5(4):507-518 ( 2001).
Siuciak et al., "Neuropharmacology" 51(2):386-396 ( 2006).
Seeger et al., "Brain Research" 985:113-126 ( 2003).
Conti et al., "Prog. Nucleic Acid Res. Mol. Biol." 63:1-38 ( 1999).
Loughney et al., "Gene" 234(1):109-117 ( 1999).
Nakazato et al., "Expert Opinion on Therapeutic Patents" 10(1):75-98 ( 2000).
Siuciak et al., "Neuropharmacology" 51(2):374-385 ( 2006).
Soderling et al., "Current Opinion Cell Biol." 12:174-179 ( 2000).
Javitt et al., "Biol. Psychiatry" 45:668-679 ( 1999).
Lewis et al., "Neuron" 28:325-333 ( 2000).
Manallack et al., "J. Med. Chem." 48(10):3449-3462 ( 2005).
Rodefer et al., "Eur. J. Neuroscience" 2:1070-1076 ( 2005).
Fujishige et al., "J. Biol. Chem." 274:18438-18445 ( 1999).
Graybiel, A. M., "Curr. Biol." 10:R509-R511 ( 2000).
Sharma et al., "Psychiatry" 174( SUPPL 28):44-51 ( 1999).
Beavo et al., "Physiol. Review" 75:725-748 ( 1995).
Soderling et al., "Proc. Natl. Acad. Sci. USA" 96(12):7071-7076 ( 1999).

* cited by examiner

*Primary Examiner* — Niloofar Rahmani
(74) *Attorney, Agent, or Firm* — George W. Johnson; Patricia S. Rocha-Tramaloni; Kimberly J. Prior

(57) ABSTRACT

The invention is concerned with novel imidazopyridine derivatives of formula (I)

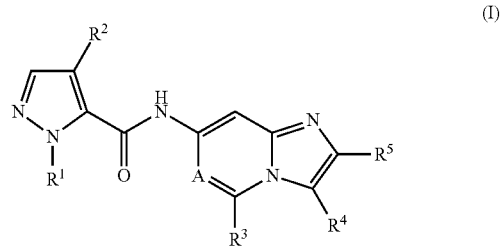

(I)

wherein $R^1$, $R^2$, $R^3$, $R^4$, $R^5$ and A are as defined in the description and in the claims, as well as physiologically acceptable salts and esters thereof. These compounds inhibit PDE10A and can be used for the treatment of various diseases, including central nervous system disorders such as Alzheimer's disease, Parkinson's disease, and schizophrenia.

18 Claims, No Drawings

SEQUENCE LISTING

```
<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 1
ggggacaagt ttgtacaaaa aagcaggctt agtacctaga ggatcaagca tttgtacttc    60
agaag                                                                65

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      PCR primer
```

```
<400> SEQUENCE: 2
ggggaccact ttgtacaaga aagctgggtc aatcttcaga tgcagctg                48
```

IMIDAZOPYRIDINES

PRIORITY TO RELATED APPLICATION(S)

This application is a division of U.S. application Ser. No. 12/886,657, filed Sep. 21, 2010; which claims the benefit of European Patent Application No. 09171253.9, filed Sep. 24, 2009. The entire contents of the above-identified applications are hereby incorporated by reference.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach, besides ameliorating positive symptoms in schizophrenic patients, poorly addresses negative and cognitive symptoms which are the best predictors of functional outcome (Sharma T., Br. J. Psychiatry, 174(suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAPM and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-1127, Soderling S. H., et al., Proc Natl Acad Sci USA (1999) 96(12):7071-7076, Loughney K., et al., Gene (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididdimal sperm (Coskran T. M, et al., J. Histochem. Cytochem. 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., Eur. J. Neuroscience 2005, 2: 1070-1076). In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The invention provides novel imidazopyridines of formula (I)

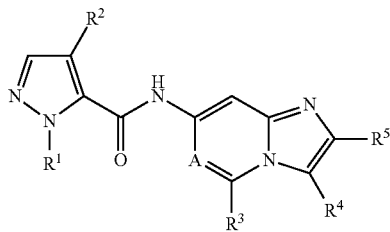

wherein
A is N or $C(R^6)$;
$R^1$ is hydrogen, lower-alkyl or fluoro-lower-alkyl;
$R^2$ is halogen, $C(O)NR^7R^8$ or $C(O)OR^9$;
$R^3$ is hydrogen, $NR^{10}R^{11}$, lower-alkyl, lower-alkoxy, fluoro-lower-alkyl or fluoro-lower-alkoxy;
$R^4$ is hydrogen, lower-alkyl, fluoro-lower-alkyl, lower alkoxy or fluoro-lower-alkoxy;
$R^5$ is aryl or heteroaryl, each of which is optionally substituted by 1 to 3 substituents independently selected from the group consisting of halogen, lower-alkyl, lower-alkoxy, fluoro-lower-alkyl, fluoro-lower-alkoxy and hydroxy;
$R^6$ is hydrogen, halogen, CN, cycloalkyl, lower-alkyl, cycloalkyl-lower-alkyl, lower-alkoxy, fluoro-lower-alkyl or fluoro-lower-alkoxy;
$R^7$ and $R^8$ are each independently selected from the group consisting of hydrogen, lower-alkyl, lower-alkoxy-lower-alkyl, fluoro-lower-alkyl, cycloalkyl, cycloalkyl-lower-alkyl, $NH_2$-lower-alkyl, N(H,lower-alkyl)-lower-alkyl, N(lower-alkyl$_2$)-lower-alkyl, hydroxy-lower-alkyl, hydroxy-lower-alkoxy-lower-alkyl, $NH_2C(O)$-lower-alkyl, N(H,lower-alkyl)C(O)-lower-alkyl, N(lower-alkyl$_2$)C(O)-lower-alkyl, lower-alkoxy, hydroxy-lower-alkyl-oxetanyl-lower-alkyl, oxo-tetrahydrofuranyl, tetrahydrofuranyl-lower-alkyl, oxo-tetrahydrofuranyl-lower-alkyl, hydroxy-fluoro-lower-alkyl, tetrahydrofuranyl, aryl and heteroaryl, wherein each aryl or heteroaryl is optionally substituted by 1 to 3 substituents independently selected from the group consisting of halogen, lower-alkyl, lower-alkoxy, fluoro-lower-alkyl, fluoro-lower-alkoxy and hydroxy, or $R^7$ and $R^8$, together with the nitrogen atom to which they are attached, form a heterocyclyl selected from the group consisting of pyrrolidinyl, azetidinyl, morpholinyl, 5,6-dihydro-8-H-[1,2,4]triazolo[4,3-a]pyrazinyl, 3,4-dihydro-1H-pyrrolo[1,2-a]pyrazinyl, 2-oxa-6-aza-spiro[3.3]heptyl, 5,6-dihydro-8H-imidazo[1,2-a]pyrazinyl, [1,4]oxazepanyl, piperazinyl, thiomorpholinyl and 2-oxa-5-aza-bicyclo[2.2.1]heptyl, which heterocyclyl is optionally substituted by 1 to 3 substituents independently selected from the group consisting of halogen, lower-alkyl, lower-alkyl-C(O), lower-alkoxy-lower-alkyl, oxo, hydroxy, hydroxy-lower-alkyl, N(lower-alkyl$_2$), $NH_2$, N(H,lower-alkyl), fluoro-lower-alkyl, fluoro-lower-alkyl-C(O), lower-alkoxy and fluoro-lower-alkoxy;
$R^9$ is hydrogen, lower-alkyl, or fluoro-lower-alkyl;
$R^{10}$ and $R^{11}$ are each independently hydrogen, lower-alkyl or fluoro-lower-alkyl,
or $R^{10}$ and $R^{11}$, together with the nitrogen atom to which they are attached, form a heterocyclyl selected from the group consisting of piperidinyl, morpholinyl, pyrrolidinyl, azetidinyl and piperazinyl, which heterocyclyl is optionally substituted by 1 to 3 substituents independently selected from the group consisting of halogen, lower-alkyl, lower-alkoxy, fluoro-lower-alkyl and fluoro-lower-alkoxy;
and pharmaceutically acceptable salts and esters thereof.

Further, the invention provides pharmaceutical compositions containing a compound of formula I or a pharmaceutically acceptable salt or ester thereof and processes for the preparation of the compounds and compositions of the invention.

Compounds of the invention are useful for the treatment of CNS diseases including, but not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the invention, in addition to being useful for the treatment of neurodegenerative disorders such as Alzheimer's disease, Huntington's disease, Parkinson's disease, multiple sclerosis, stroke and spinal cord injury, may be useful for the treatment of solid tumors and hematological malignancies such as renal cell carcinoma or breast cancer.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "hydroxy-lower-alkyl" refers to a lower-alkyl group as defined above, which is substituted by 1 to 3 hydroxy groups. Examples of hydroxy-lower-alkyl groups are e.g. hydroxy-methyl, hydroxy-ethyl, hydroxy propyl, 3-hydroxy-propyl, 2-hydroxy-propyl, 3-hydroxy-prop-2-yl, 2,3-dihydroxy-propyl and 1,3-dihydroxy-prop-2-yl.

The term "hydroxy-lower-alkoxy" refers to a lower-alkoxy group as defined above, which is substituted by 1 to 3 hydroxy groups. Examples of hydroxy-lower-alkoxy groups are e.g. hydroxy-methoxy, hydroxy-ethoxy, hydroxy-propoxy, 3-hydroxy-propoxy, 2-hydroxy-propoxy, 3-hydroxy-prop-2-oxy, 2,3-dihydroxy-propoxy and 1,3-dihydroxy-prop-2-oxy.

The term "hydroxy-fluoro-lower-alkyl" refers to a fluoro-lower-alkoxy group as defined above, which is substituted by 1 to 3 hydroxy groups. Examples of hydroxy-fluoro-lower-alkoxy groups are e.g. 2,2,2-trifluoro-1-hydroxy-ethyl, 3,3,3-trifluoro-2-hydroxy-propyl.

The term "aryl", alone or in combination, denotes a phenyl or naphthyl group, preferably a phenyl group, which is optionally substituted, unless specifically stated otherwise, by 1 to 5, preferably 1 to 3, substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, (H,lower-alkyl)NC(O), (lower-alkyl)$_2$NC(O), fluoro-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, heteroaryl, cycloalkyl, phenyl and phenyloxy. Preferred substituents can be halogen, lower-alkyl, lower-alkoxy, fluoro-lower-alkyl and fluoro-lower-alkoxy. Furthermore, aryl groups can preferably be substituted as described in the description and claims below.

The term "heteroaryl" refers to an aromatic 5 to 6 membered monocyclic ring or 9 to 10 membered bicyclic ring system which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl and isoquinolinyl. Preferred heteroaryl groups are pyridinyl or thiazolyl. Unless specifically stated otherwise, a heteroaryl group may optionally have a substitution pattern as described earlier in connection with the term "aryl". Furthermore, heteroaryl groups can preferably be substituted as described in the description and claims below.

"Pharmaceutically acceptable," such as pharmaceutically acceptable carrier, excipient, etc., means pharmacologically acceptable and substantially non-toxic to the subject to which the particular compound is administered.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na-, K-, Ca- and trimethylammoniumsalt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Therapeutically effective amount" means an amount that is effective to prevent, alleviate or ameliorate symptoms of disease or prolong the survival of the subject being treated.

In detail, the present invention provides compounds of formula (I)

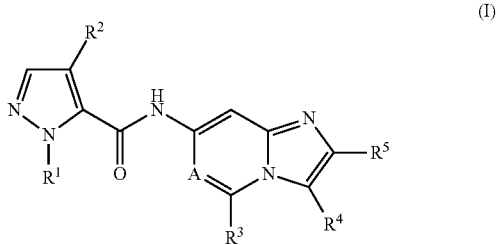

(I)

wherein

A is N or C($R^6$);

$R^1$ is hydrogen, lower-alkyl or fluoro-lower-alkyl;

$R^2$ is halogen, C(O)N$R^7R^8$ or C(O)O$R^9$;

$R^3$ is hydrogen, N$R^{10}R^{11}$, lower-alkyl, lower-alkoxy, fluoro-lower-alkyl or fluoro-lower-alkoxy;

$R^4$ is hydrogen, lower-alkyl, fluoro-lower-alkyl, lower alkoxy or fluoro-lower-alkoxy;

$R^5$ is aryl or heteroaryl, each of which is optionally substituted by 1 to 3 substituents independently selected from the group consisting of halogen, lower-alkyl, lower-alkoxy, fluoro-lower-alkyl, fluoro-lower-alkoxy and hydroxy;

$R^6$ is hydrogen, halogen, CN, cycloalkyl, lower-alkyl, cycloalkyl-lower-alkyl, lower-alkoxy, fluoro-lower-alkyl or fluoro-lower-alkoxy;

$R^7$ and $R^8$ are each independently selected from the group consisting of hydrogen, lower-alkyl, lower-alkoxy-lower-alkyl, fluoro-lower-alkyl, cycloalkyl, cycloalkyl-lower-alkyl, NH$_2$-lower-alkyl, N(H,lower-alkyl)-lower-alkyl, N(lower-alkyl$_2$)-lower-alkyl, hydroxy-lower-alkyl, hydroxy-lower-alkoxy-lower-alkyl, NH$_2$C(O)-lower-alkyl, N(H,lower-alkyl)C(O)-lower-alkyl, N(lower-alkyl$_2$)C(O)-lower-alkyl, lower-alkoxy, hydroxy-lower-alkyl-oxetanyl-lower-alkyl, oxo-tetrahydrofuranyl, tetrahydrofuranyl-lower-alkyl, oxo-tetrahydrofuranyl-lower-alkyl, hydroxy-fluoro-lower-alkyl, tetrahydrofuranyl, aryl and heteroaryl, wherein each aryl or heteroaryl is optionally substituted by 1 to 3 substituents independently selected from the group consisting of halogen, lower-alkyl, lower-alkoxy, fluoro-lower-alkyl, fluoro-lower-alkoxy and hydroxy, or $R^7$ and $R^8$, together with the nitrogen atom to which they are attached, form a heterocyclyl selected from the group consisting of pyrrolidinyl, azetidinyl, morpholinyl, 5,6-dihydro-8-H-[1,2,4]triazolo[4,3-a]pyrazinyl, 3,4-dihydro-1H-pyrrolo[1,2-a]pyrazinyl, 2-oxa-6-aza-spiro[3.3]heptyl, 5,6-dihydro-8H-imidazo[1,2-a]pyrazinyl, [1,4]oxazepanyl, piperazinyl, thiomorpholinyl and 2-oxa-5-aza-bicyclo[2.2.1]heptyl, which heterocyclyl is optionally substituted by 1 to 3 substituents independently selected from the group consisting of halogen, lower-alkyl, lower-alkyl-C(O), oxo, hydroxy, hydroxy-lower-alkyl, N(lower-alkyl$_2$), NH$_2$, N(H,lower-alkyl), fluoro-lower-alkyl, fluoro-lower-alkyl-C(O), lower-alkoxy and fluoro-lower-alkoxy;

$R^9$ is hydrogen, lower-alkyl, or fluoro-lower-alkyl;

$R^{10}$ and $R^{11}$ are each independently hydrogen, lower-alkyl or fluoro-lower-alkyl, or $R^{10}$ and $R^{11}$, together with the nitrogen atom to which they are attached, form a heterocyclyl selected from the group consisting of piperidinyl, morpholinyl, pyrrolidinyl, azetidinyl and piperazinyl, which heterocyclyl is optionally substituted by 1 to 3 substituents independently selected from the group consisting of halogen, lower-alkyl, lower-alkoxy, fluoro-lower-alkyl and fluoro-lower-alkoxy;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

In one embodiment the present invention provides compounds of formula (I) as described above, wherein A is N. In another embodiment, the compounds are those, wherein A is C($R^6$) and $R^6$ is as defined above. Preferably, $R^1$ is hydrogen or lower alkyl, more preferably methyl.

In one embodiment the present invention provides compounds of formula (I) as described above, wherein $R^2$ is C(O)N$R^7R^8$ and $R^7$ and $R^8$ are as defined above. It is furthermore preferred, that $R^3$ is hydrogen or N$R^{10}R^{11}$ and $R^{10}$ and $R^{11}$ are as defined above. Compounds, wherein $R^3$ is hydrogen, are particularly preferred.

In another embodiment of the present invention, $R^4$ is hydrogen or lower-alkyl, more preferably hydrogen. Moreover, it is preferred that $R^5$ is phenyl or thiazolyl, each of which is optionally substituted by 1 to 2 substituents independently selected from halogen. More preferably, $R^5$ is phenyl.

Other preferred compounds according to the present invention are those, wherein $R^6$ is hydrogen, halogen, CN or cycloalkyl, particularly those, wherein $R^6$ is hydrogen, CN, bromo, chloro or cyclopropyl.

Other preferred compounds of the present invention are those, wherein $R^7$ and $R^8$ are each independently selected from the group consisting of hydrogen, lower-alkyl, lower-alkoxy-lower-alkyl, fluoro-lower-alkyl, cycloalkyl, N(H, lower-alkyl)-lower-alkyl, hydroxy-lower-alkyl, hydroxy-lower-alkoxy-lower-alkyl, N(lower-alkyl$_2$)C(O)-lower-alkyl, lower-alkoxy, 3-(hydroxy-lower-alkyl)-oxetan-3-yl-lower-alkyl, 2-oxo-tetrahydrofuranyl, tetrahydrofuranyl-lower-alkyl, hydroxy-fluoro-lower-alkyl, tetrahydrofuranyl, phenyl and pyridinyl, or $R^7$ and $R^8$, together with the nitrogen atom to which they are attached, form a heterocyclyl selected from the group consisting of pyrrolidinyl, azetidinyl, morpholinyl, 5,6-dihydro-8-H-[1,2,4]triazolo[4,3-a]pyrazinyl, 3,4-dihydro-1H-pyrrolo[1,2-a]pyrazinyl, 2-oxa-6-aza-spiro[3.3]heptyl, 5,6-dihydro-8H-imidazo[1,2-a]pyrazinyl, [1,4]oxazepanyl, piperazinyl, thiomorpholinyl and 2-oxa-5-aza-bicyclo[2.2.1]heptyl, which heterocyclyl is optionally substituted by 1 to 3 substituents independently selected from the group consisting of halogen, lower-alkyl, lower-alkyl-C(O), lower-alkoxy-lower-alkyl, oxo, hydroxy, hydroxy-lower-alkyl, N(lower-alkyl$_2$). Preferably, $R^7$ and $R^8$ are each independently selected from the group consisting of hydrogen, lower-alkyl, lower-alkoxy-lower-alkyl and hydroxy-lower-alkyl, or $R^7$ and $R^8$, together with the nitrogen atom to which they are attached, form a heterocyclyl selected from the group consisting of azetidinyl and morpholinyl, which heterocyclyl is optionally substituted by 1 to 2 substituents independently selected from the group consisting of halogen and hydroxy. More preferably, $R^7$ and $R^8$ are each independently selected from the group consisting of hydrogen, methyl, 3-methoxypropyl and 3-hydroxy-propyl, or $R^7$ and $R^8$, together with the nitrogen atom to which they are attached, form 3,3-difluoro-azetidin-1-yl, morpholin-4-yl, azetidin-1-yl or 3-hydroxy-azetidin-1-yl.

In another embodiment of the present invention provides compounds as defined above, wherein $R^9$ is lower-alkyl. Other preferred compounds of the present invention are those, wherein $R^{10}$ and $R^{11}$, together with the nitrogen atom to which they are attached, form piperidinyl or morpholinyl.

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:

4-Chloro-2-methyl-2H-pyrazole-3-carboxylic acid (2-phenyl-imidazo[1,2-a]pyridin-7-yl)-amide, 2-Methyl-2H-pyrazole-3,4-dicarboxylic acid 4-amide 3-[(2-phenyl-imidazo[1,2-a]pyridin-7-yl)-amide], 2-Methyl-2H-pyrazole-3,4-dicarboxylic acid 4-dimethylamide 3-[(2-phenyl-imidazo[1,2-a]pyridin-7-yl)-amide], 2-Methyl-2H-pyrazole-3,4-dicarboxylic acid 4-dimethylamide 3-{[2-(4-fluoro-phenyl)-imidazo[1,2-a]pyridin-7-yl]-amide}, 4-Chloro-2-methyl-2H-pyrazole-3-carboxylic acid (2-thiazol-2-yl-imidazo[1,2-a]pyridin-7-yl)-amide, 2-Methyl-2H-pyrazole-3,4-dicarboxylic acid 4-methylamide 3-[(2-phenyl-imidazo[1,2-a]pyridin-7-yl)-amide], 2-Methyl-2H-pyrazole-3,4-dicarboxylic acid 4-dimethylamide 3-{[2-(3-fluoro-phenyl)-imidazo[1,2-a]pyridin-7-yl]-amide}, 2-Methyl-2H-pyrazole-3,4-dicarboxylic acid 4-dimethylamide 3-[(2-thiazol-2-yl-imidazo[1,2-a]pyridin-7-yl)-amide], 4-Chloro-2-methyl-2H-pyrazole-3-carboxylic acid (3-methyl-2-phenyl-imidazo[1,2-a]pyridin-7-yl)-amide, 1-Methyl-5-(2-phenyl-imidazo[1,2-a]pyridin-7-ylcarbamoyl)-1H-pyrazole-4-carboxylic acid ethyl ester, 5-(2-Phenyl-imidazo[1,2-a]pyridin-7-ylcarbamoyl)-1H-pyrazole-4-carboxylic acid ethyl ester, 1-Ethyl-5-(2-phenyl-imidazo[1,2-a]pyridin-7-ylcarbamoyl)-1H-pyrazole-4-carboxylic acid ethyl ester, 2-Methyl-4-(pyrrolidine-1-carbonyl)-2H-pyrazole-3-carboxylic acid (2-phenyl-imidazo[1,2-a]pyridin-7-yl)-amide, 5-(6-Cyano-2-phenyl-imidazo[1,2-a]pyridin-7-ylcarbamoyl)-1-methyl-1H-pyrazole-4-carboxylic acid ethyl ester, 2-Methyl-2H-pyrazole-3,4-dicarboxylic acid 4-(methyl-propyl-amide) 3-[(2-phenyl-imidazo[1,2-a]pyridin-7-yl)-amide], 2-Methyl-2H-pyrazole-3,4-dicarboxylic acid 4-[(2-methoxy-ethyl)-methyl-amide]3-[(2-phenyl-imidazo[1,2-a]pyridin-7-yl)-amide], 4-(3,3-Difluoro-azetidine-1-carbonyl)-2-methyl-2H-pyrazole-3-carboxylic acid (2-phenyl-imidazo[1,2-a]pyridin-7-yl)-amide, 2-Methyl-2H-pyrazole-3,4-dicarboxylic acid 3-[(2-phenyl-imidazo[1,2-a]pyridin-7-yl)-amide]-4-[(2,2,2-trifluoro-ethyl)-amide], 2-Methyl-2H-pyrazole-3,4-dicarboxylic acid 4-cyclopropylamide 3-[(2-phenyl-imidazo[1,2-a]pyridin-7-yl)-amide], 2-Methyl-4-(morpholine-4-carbonyl)-2H-pyrazole-3-carboxylic acid (2-phenyl-imidazo[1,2-a]pyridin-7-yl)-amide, 2-Methyl-2H-pyrazole-3,4-dicarboxylic acid 4-[methyl-(2-methylamino-ethyl)-amide]3-[(2-phenyl-imidazo[1,2-a]pyridin-7-yl)-amide], 2-Methyl-2H-pyrazole-3,4-dicarboxylic acid 4-diethylamide 3-[(2-phenyl-imidazo[1,2-a]pyridin-7-yl)-amide], 2-Methyl-2H-pyrazole-3,4-dicarboxylic acid 4-[(2-hydroxy-ethyl)-amide]3-[(2-phenyl-imidazo[1,2-a]pyridin-7-yl)-amide], 2-Methyl-2H-pyrazole-3,4-dicarboxylic acid 4-tert-butylamide 3-[(2-phenyl-imidazo[1,2-a]pyridin-7-yl)-amide], 2-Methyl-2H-pyrazole-3,4-dicarboxylic acid 4-isopropylamide 3-[(2-phenyl-imidazo[1,2-a]pyridin-7-yl)-amide], 4-(Azetidine-1-carbonyl)-2-methyl-2H-pyrazole-3-carboxylic acid (2-phenyl-imidazo[1,2-a]pyridin-7-yl)-amide, 4-(5,6-Dihydro-8H-[1,2,4]triazolo[4,3-a]pyrazine-7-carbonyl)-2-methyl-2H-pyrazole-3-carboxylic acid (2-phenyl-imidazo[1,2-a]pyridin-7-yl)-amide, 2-Methyl-2H-pyrazole-3,4-dicarboxylic acid 4-[(3-methoxy-propyl)-amide]3-[(2-phenyl-imidazo[1,2-a]pyridin-7-yl)-amide], 2-Methyl-2H-pyrazole-3,4-dicarboxylic acid 4-[(3-hydroxy-propyl)-amide]3-[(2-phenyl-imidazo[1,2-a]pyridin-7-yl)-amide], 2-Methyl-2H-pyrazole-3,4-dicarboxylic acid 4-{[2-(2-hydroxy-ethoxy)-ethyl]-amide}3-[(2-phenyl-imidazo[1,2-a]pyridin-7-yl)-amide], 2-Methyl-2H-pyrazole-3,4-dicarboxylic acid 4-dimethylcarbamoylmethyl-amide 3-[(2-phenyl-imidazo[1,2-a]pyridin-7-yl)-amide], 2-Methyl-2H-pyrazole-3,4-dicarboxylic acid 4-(methoxymethyl-amide) 3-[(2-phenyl-imidazo[1,2-a]pyridin-7-yl)-amide], 2-Methyl-2H-pyrazole-3,4-dicarboxylic acid 4-[(3-hydroxymethyl-oxetan-3-ylmethyl)-amide]3-[(2-phenyl-imidazo[1,2-a]pyridin-7-yl)-amide], 2-Methyl-2H-pyrazole-3,4-dicarboxylic acid 4-[(2-oxo-tetrahydro-furan-3-yl)-amide]3-[(2-phenyl-imidazo[1,2-a]pyridin-7-yl)-amide], 2-Methyl-2H-pyrazole-3,4-dicarboxylic acid 4-[(2-hydroxy-propyl)-amide]3-[(2-phenyl-imidazo[1,2-a]pyridin-7-yl)-amide], 2-Methyl-2H-pyrazole-3,4-dicarboxylic acid 4-[(2-hydroxy-1-methyl-ethyl)-amide]3-[(2-phenyl-imidazo[1,2-a]pyridin-7-yl)-amide], 2-Methyl-2H-pyrazole-3,4-dicarboxylic acid 3-[(2-phenyl-imidazo[1,2-a]pyridin-7-yl)-amide]-4-[(tetrahydro-furan-2-ylmethyl)-amide], 2-Methyl-4-(1-methyl-3,4-dihydro-1H-pyrrolo[1,2-a]pyrazine-2-carbonyl)-2H-pyrazole-3-carboxylic acid (2-phenyl-imidazo[1,2-a]pyridin-7-yl)-amide, 2-Methyl-2H-pyrazole-3,4-dicarboxylic acid 3-[(2-phenyl-imidazo[1,2-a]pyridin-7-yl)-amide]-4-[(3,3,3-trifluoro-2-hydroxy-propyl)-amide], 2-Methyl-2H-pyrazole-3,4-dicarboxylic acid 3-[(2-phenyl-imidazo[1,2-a]pyridin-7-yl)-amide]-4-[(tetrahydro-furan-3-ylmethyl)-amide], 2-Methyl-2H-pyrazole-3,4-dicarboxylic acid 3-[(2-phenyl-imidazo[1,2-a]pyridin-7-yl)-amide]-4-[(tetrahydro-furan-3-yl)-amide], 2-Methyl-4-(2-oxa-6-aza-spiro[3.3]heptane-6-carbonyl)-2H-pyrazole-3-carboxylic acid (2-phenyl-imidazo[1,2-a]pyridin-7-yl)-amide, 4-(5,6-Dihydro-8H-imidazo[1,2-a]pyrazine-7-carbonyl)-2-methyl-2H-pyrazole-3-carboxylic acid (2-phenyl-imidazo[1,2-a]pyridin-7-yl)-amide, 2-Methyl-4-([1,4]oxazepane-4-carbonyl)-2H-pyrazole-3-carboxylic acid (2-phenyl-imidazo[1,2-a]pyridin-7-yl)-amide, 4-(4-Acetyl-piperazine-1-carbonyl)-2-methyl-2H-pyrazole-3-carboxylic acid (2-phenyl-imidazo[1,2-a]pyridin-7-yl)-amide, 2-Methyl-4-(piperazine-1-carbonyl)-2H-pyrazole-3-carboxylic acid (2-phenyl-imidazo[1,2-a]pyridin-7-yl)-amide, 4-((S)-2-Methoxymethyl-pyrrolidine-1-carbonyl)-2-methyl-2H-pyrazole-3-carboxylic acid (2-phenyl-imidazo[1,2-a]pyridin-7-yl)-amide, 4-(1,1-Dioxo-thiomorpholine-4-carbonyl)-2-methyl-2H-pyrazole-3-carboxylic acid (2-phenyl-imidazo[1,2-a]pyridin-7-yl)-amide, 2-Methyl-4-(3-oxo-piperazine-1-carbonyl)-2H-pyrazole-3-carboxylic acid (2-phenyl-imidazo[1,2-a]pyridin-7-yl)-amide, 4-(3-Hydroxy-azetidine-1-carbonyl)-2-methyl-2H-pyrazole-3-carboxylic acid (2-phenyl-imidazo[1,2-a]pyridin-7-yl)-amide,
2-Methyl-4-((1S,4S)-2-oxa-5-aza-bicyclo[2.2.1]heptane-5-carbonyl)-2H-pyrazole-3-carboxylic acid (2-phenyl-imidazo[1,2-a]pyridin-7-yl)-amide,
2-Methyl-4-(4-methyl-piperazine-1-carbonyl)-2H-pyrazole-3-carboxylic acid (2-phenyl-imidazo[1,2-a]pyridin-7-yl)-amide,
4-(3-Hydroxymethyl-morpholine-4-carbonyl)-2-methyl-2H-pyrazole-3-carboxylic acid (2-phenyl-imidazo[1,2-a]pyridin-7-yl)-amide,
2-Methyl-2H-pyrazole-3,4-dicarboxylic acid 4-phenylamide 3-[(2-phenyl-imidazo[1,2-a]pyridin-7-yl)-amide],
2-Methyl-2H-pyrazole-3,4-dicarboxylic acid 3-[(2-phenyl-imidazo[1,2-a]pyridin-7-yl)-amide]-4-pyridin-4-ylamide,
2-Methyl-2H-pyrazole-3,4-dicarboxylic acid 4-[bis-(2-hydroxy-ethyl)-amide]3-[(2-phenyl-imidazo[1,2-a]pyridin-7-yl)-amide],
2-Methyl-2H-pyrazole-3,4-dicarboxylic acid 4-[(1-hydroxymethyl-propyl)-amide]3-[(2-phenyl-imidazo[1,2-a]pyridin-7-yl)-amide],
4-(3-Hydroxy-pyrrolidine-1-carbonyl)-2-methyl-2H-pyrazole-3-carboxylic acid (2-phenyl-imidazo[1,2-a]pyridin-7-yl)-amide,
4-(3-Dimethylamino-pyrrolidine-1-carbonyl)-2-methyl-2H-pyrazole-3-carboxylic acid (2-phenyl-imidazo[1,2-a]pyridin-7-yl)-amide,
2-Methyl-2H-pyrazole-3,4-dicarboxylic acid 4-[(2,3-dihydroxy-propyl)-methyl-amide]3-[(2-phenyl-imidazo[1,2-a]pyridin-7-yl)-amide],
2-Methyl-2H-pyrazole-3,4-dicarboxylic acid 4-[(2-methoxy-ethyl)-amide]3-[(2-phenyl-imidazo[1,2-a]pyridin-7-yl)-amide],
4-(Azetidine-1-carbonyl)-2-ethyl-2H-pyrazole-3-carboxylic acid (2-phenyl-imidazo[1,2-a]pyridin-7-yl)-amide,
4-Chloro-2-methyl-2H-pyrazole-3-carboxylic acid (5-morpholin-4-yl-2-phenyl-imidazo[1,2-c]pyrimidin-7-yl)-amide,
2-Methyl-2H-pyrazole-3,4-dicarboxylic acid 3-{[2-(3-chloro-phenyl)-imidazo[1,2-a]pyridin-7-yl]-amide}-4-dimethylamide,
2H-Pyrazole-3,4-dicarboxylic acid 4-methylamide 3-[(2-phenyl-imidazo[1,2-a]pyridin-7-yl)-amide],
2-Methyl-2H-pyrazole-3,4-dicarboxylic acid 4-[(2-hydroxy-1-hydroxymethyl-ethyl)-amide]3-[(2-phenyl-imidazo[1,2-a]pyridin-7-yl)-amide],
4-(Azetidine-1-carbonyl)-2-methyl-2H-pyrazole-3-carboxylic acid (6-bromo-2-phenyl-imidazo[1,2-a]pyridin-7-yl)-amide,
4-(Azetidine-1-carbonyl)-2-methyl-2H-pyrazole-3-carboxylic acid (6-cyano-2-phenyl-imidazo[1,2-a]pyridin-7-yl)-amide,
2-Methyl-4-(morpholine-4-carbonyl)-2H-pyrazole-3-carboxylic acid (6-cyano-2-phenyl-imidazo[1,2-a]pyridin-7-yl)-amide,
4-(Azetidine-1-carbonyl)-2-methyl-2H-pyrazole-3-carboxylic acid (6-chloro-2-phenyl-imidazo[1,2-a]pyridin-7-yl)-amide,
4-(Azetidine-1-carbonyl)-2-methyl-2H-pyrazole-3-carboxylic acid (2-phenyl-5-piperidin-1-yl-imidazo[1,2-c]pyrimidin-7-yl)-amide,
2-Methyl-4-(morpholine-4-carbonyl)-2H-pyrazole-3-carboxylic acid (6-chloro-2-phenyl-imidazo[1,2-a]pyridin-7-yl)-amide,
2-Methyl-4-(morpholine-4-carbonyl)-2H-pyrazole-3-carboxylic acid (5-morpholin-4-yl-2-phenyl-imidazo[1,2-c]pyrimidin-7-yl)-amide,
4-(Azetidine-1-carbonyl)-2-methyl-2H-pyrazole-3-carboxylic acid (6-cyclopropyl-2-phenyl-imidazo[1,2-a]pyridin-7-yl)-amide,
2-Methyl-4-(morpholine-4-carbonyl)-2H-pyrazole-3-carboxylic acid (6-cyclopropyl-2-phenyl-imidazo[1,2-a]pyridin-7-yl)-amide,
4-(Azetidine-1-carbonyl)-2-methyl-2H-pyrazole-3-carboxylic acid (5-morpholin-4-yl-2-phenyl-imidazo[1,2-c]pyrimidin-7-yl)-amide,
2-Methyl-2H-pyrazole-3,4-dicarboxylic acid 3-[(6-cyano-2-phenyl-imidazo[1,2-a]pyridin-7-yl)-amide]-4-[(3-hydroxy-propyl)-amide],
2-Methyl-4-(piperazine-1-carbonyl)-2H-pyrazole-3-carboxylic acid (6-cyano-2-phenyl-imidazo[1,2-a]pyridin-7-yl)-amide,
2-Methyl-2H-pyrazole-3,4-dicarboxylic acid 3-[(6-cyano-2-phenyl-imidazo[1,2-a]pyridin-7-yl)-amide]-4-[(2-hydroxy-propyl)-amide],
4-Chloro-2-methyl-2H-pyrazole-3-carboxylic acid (2-phenyl-imidazo[1,2-c]pyrimidin-7-yl)-amide,
2-Methyl-2H-pyrazole-3,4-dicarboxylic acid 4-amide 3-[(2-phenyl-imidazo[1,2-c]pyrimidin-7-yl)-amide],
2-Methyl-2H-pyrazole-3,4-dicarboxylic acid 4-dimethylamide 3-[(2-phenyl-imidazo[1,2-c]pyrimidin-7-yl)-amide],
1-Methyl-5-(2-phenyl-imidazo[1,2-c]pyrimidin-7-ylcarbamoyl)-1H-pyrazole-4-carboxylic acid ethyl ester,
2-Methyl-2H-pyrazole-3,4-dicarboxylic acid 4-methylamide 3-[(2-phenyl-imidazo[1,2-c]pyrimidin-7-yl)-amide],
2-Methyl-2H-pyrazole-3,4-dicarboxylic acid 4-[(3-methoxy-propyl)-amide]3-[(2-phenyl-imidazo[1,2-c]pyrimidin-7-yl)-amide],
4-(Azetidine-1-carbonyl)-2-methyl-2H-pyrazole-3-carboxylic acid (2-phenyl-imidazo[1,2-c]pyrimidin-7-yl)-amide,
2-Methyl-2H-pyrazole-3,4-dicarboxylic acid 4-isopropylamide 3-[(2-phenyl-imidazo[1,2-c]pyrimidin-7-yl)-amide],
2-Methyl-2H-pyrazole-3,4-dicarboxylic acid 4-[(2-hydroxy-ethyl)-amide]3-[(2-phenyl-imidazo[1,2-c]pyrimidin-7-yl)-amide], and
2-Methyl-4-(morpholine-4-carbonyl)-2H-pyrazole-3-carboxylic acid (2-phenyl-imidazo[1,2-c]pyrimidin-7-yl)-amide
and pharmaceutically acceptable salts and esters thereof.

Particularly preferred compounds of formula (I) are those selected from the group consisting of:
2-Methyl-2H-pyrazole-3,4-dicarboxylic acid 4-dimethylamide 3-[(2-phenyl-imidazo[1,2-a]pyridin-7-yl)-amide],
4-(3,3-Difluoro-azetidine-1-carbonyl)-2-methyl-2H-pyrazole-3-carboxylic acid (2-phenyl-imidazo[1,2-a]pyridin-7-yl)-amide,
2-Methyl-4-(morpholine-4-carbonyl)-2H-pyrazole-3-carboxylic acid (2-phenyl-imidazo[1,2-a]pyridin-7-yl)-amide,
4-(Azetidine-1-carbonyl)-2-methyl-2H-pyrazole-3-carboxylic acid (2-phenyl-imidazo[1,2-a]pyridin-7-yl)-amide,
2-Methyl-2H-pyrazole-3,4-dicarboxylic acid 4-[(3-methoxy-propyl)-amide]3-[(2-phenyl-imidazo[1,2-a]pyridin-7-yl)-amide],
2-Methyl-2H-pyrazole-3,4-dicarboxylic acid 4-[(3-hydroxy-propyl)-amide]3-[(2-phenyl-imidazo[1,2-a]pyridin-7-yl)-amide], 2-Methyl-2H-pyrazole-3,4-dicarboxylic acid 4-[(2-hydroxy-propyl)-amide]3-[(2-phenyl-imidazo[1,2-a]pyridin-7-yl)-amide], 2-Methyl-2H-pyrazole-3,4-dicarboxylic acid 4-[(2-hydroxy-1-methyl-ethyl)-amide]3-[(2-phenyl-imidazo[1,2-a]pyridin-7-yl)-amide], 4-(3-Hydroxy-azetidine-1-carbonyl)-2-methyl-2H-pyrazole-3-carboxylic acid (2-phenyl-imidazo[1,2-a]pyridin-7-yl)-amide, 4-(Azetidine-1-carbonyl)-2-methyl-2H-pyrazole-3-carboxylic acid (6-bromo-2-phenyl-imidazo[1,2-a]pyridin-7-yl)-amide, 2-Methyl-4-(morpholine-4-carbonyl)-2H-pyrazole-3-carboxylic acid (6-cyano-2-phenyl-imidazo[1,2-a]pyridin-7-yl)-amide, 4-(Azetidine-1-carbonyl)-2-methyl-2H-pyrazole-3-carboxylic acid (6-chloro-2-phenyl-imidazo[1,2-a]pyridin-7-yl)-amide, 2-Methyl-4-(morpholine-4-carbonyl)-2H-pyrazole-3-carboxylic acid (6-chloro-2-phenyl-imidazo[1,2-a]pyridin-7-yl)-amide, 4-(Azetidine-1-carbonyl)-2-methyl-2H-pyrazole-3-carboxylic acid (6-cyclopropyl-2-phenyl-imidazo[1,2-a]pyridin-7-yl)-amide, 2-Methyl-4-(morpholine-4-carbonyl)-2H-pyrazole-3-carboxylic acid (6-cyclopropyl-2-phenyl-imidazo[1,2-a]pyridin-7-yl)-amide, 2-Methyl-2H-pyrazole-3,4-dicarboxylic acid 4-dimethylamide 3-[(2-phenyl-imidazo[1,2-c]pyrimidin-7-yl)-amide], 2-Methyl-2H-pyrazole-3,4-dicarboxylic acid 4-[(3-methoxy-propyl)-amide]3-[(2-phenyl-imidazo[1,2-c]pyrimidin-7-yl)-amide], 4-(Azetidine-1-carbonyl)-2-methyl-2H-pyrazole-3-carboxylic acid (2-phenyl-imidazo[1,2-c]pyrimidin-7-yl)-amide, and 2-Methyl-4-(morpholine-4-carbonyl)-2H-pyrazole-3-carboxylic acid (2-phenyl-imidazo[1,2-c]pyrimidin-7-yl)-amide and pharmaceutically acceptable salts and esters thereof.

It will be appreciated that the compounds of general formula (I) in this invention can be derivatised at functional groups to provide derivatives which are capable of conversion back to the parent compound in vivo.

The invention further provides a process for the manufacture of compounds of formula (I) as defined above, which process comprises reacting a compound of formula (II)

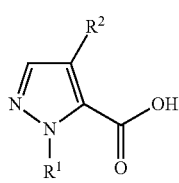

(II)

with a compound of formula (III)

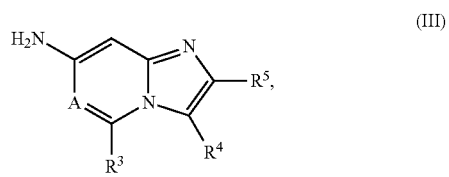

(III)

wherein $R^1$, $R^2$, $R^3$, $R^4$, $R^5$ and A are as defined above.

The reaction of a compound of formula (II) with a compound of formula (III) can be carried out under conditions as described in the examples or under conditions well known to the person skilled in the art. For example, the reaction can be performed in solvents like dimethylformamide (DMF), tetrahydrofurane (THF), dioxane, dichloromethane, ethyl acetate, 1-methyl-2-pyrolidone (NMP) and the like at temperatures in the range of e.g. at −10-120° C., but typically at 0° C.-room temperature, at atmospheric pressure or elevated pressure. The reaction can be carried out in one step or in several steps. If the reaction is carried out in one step, the conversion is usually accomplished with a coupling reagent, such as N,N'-dicyclohexylcarbodiimide (DCC), N-(3-dimethylaminopropyl)-N'-ethylcarbodiimide hydrochloride (EDC), 2-(1H-benzotriazole-1-yl)-1,1,3,3-tetramethyluronium tetrafluoroborate (TBTU), propylphosphonic anhydride, and the like (a large number of chemically diverse coupling reagents are described in the literature). If the reaction is carried out in several steps, the acid (II) is usually transformed into a reactive species such as an acid chloride or an acid anhydride, for instance by reaction with thionyl chloride, sulphuryl chloride, phosphoroxychloride, oxalylchloride, or the like, with or without a solvent such as dichloromethane, with or without an additive such as DMF. This is then converted in another step by addition of the amine (III) into the product (I). The second step is typically carried out in a solvent such as dimethylformamide (DMF), tetrahydrofurane (THF), dioxane, dichloromethane, ethyl acetate, 1-methyl-2-pyrolidone (NMP) and the like at temperatures in the range of e.g. at −10-120° C., but typically at 0° C.-room temperature, at atmospheric pressure or elevated pressure. It is often advantageous to add a base, such as triethylamine or diisopropylethylamine, to the reaction mixture.

The compounds of formula (II) and (III) can be prepared by methods known in the art or as described below or in analogy thereto. Unless otherwise indicated, $R^1$, $R^2$, $R^3$, $R^4$, $R^5$ and A are as described above.

The present invention also relates to compounds of formula (I) as defined above, when prepared by a process as described above.

Compounds of formula 1 can be prepared from building blocks 2 and 3 according to Scheme 1. The conversion, commonly known as amide coupling, can be achieved in several ways. In one method, the acid 2 is activated with a coupling reagent, such as 2-(1H-benzotriazole-1-yl)-1,1,3,3-tetramethyluronium tetrafluoroborate (TBTU), and converted by addition of amine 3 to the desired product, 1. In another method, the acid 2 is activated by transformation into an acid chloride, e.g. by reaction with thionyl chloride. The acid chloride is then converted by addition of the amine 3 to the desired product, 1. A base, e.g. diisopropylethylamine (DIPEA), is usually added to bind liberated HCl.

Scheme 1

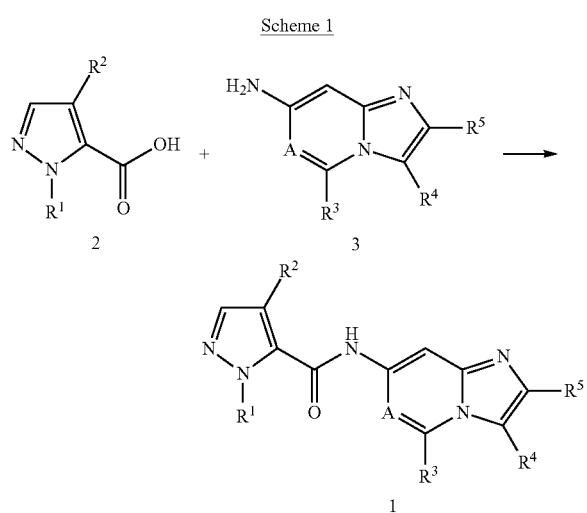

Compounds of formula 3 can be prepared according to Scheme 2: A compound of the general formula 4, such as a (substituted) 2-amino-isonicotinic acid ester, is reacted with a compound 5, such as a (substituted) 2-bromoacetophenone, with a suitable base, such as $NaHCO_3$, to give 6 (step a). Ester 6 is then saponified, e.g. by reaction with KOH (step b). The obtained acid 7 is then subjected to a rearrangement-degradation reaction to yield a carbamate 8 (step c). Many variants of such a rearrangement-degradation reaction are known; for instance, if step c is accomplished by a treatment with diphenylphosphoryl azide and a base in tert-butanol, a Boc-protected amine 8 ($R^{14}$=tBu) is obtained. These latter conditions are a variant of a reaction known as the Curtius degradation. The obtained carbamate 8 can then be transformed into an amine by suitable reaction conditions depending on the nature of $R^{14}$ (step d); e.g., if $R^{14}$=tBu, the transformation can usually be accomplished by treatment with acid, e.g. trifluoroacetic acid. Alternatively, compounds of formula 3 can be prepared from pyridinediamines or pyrimidinediamines 9 by reaction with 5, and a suitable base, such as $NaHCO_3$ (step e).

Scheme 2

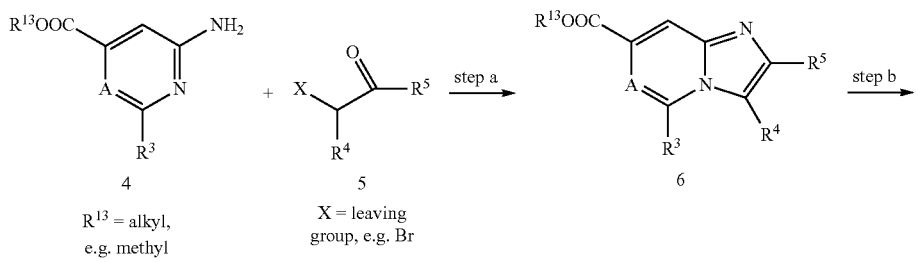

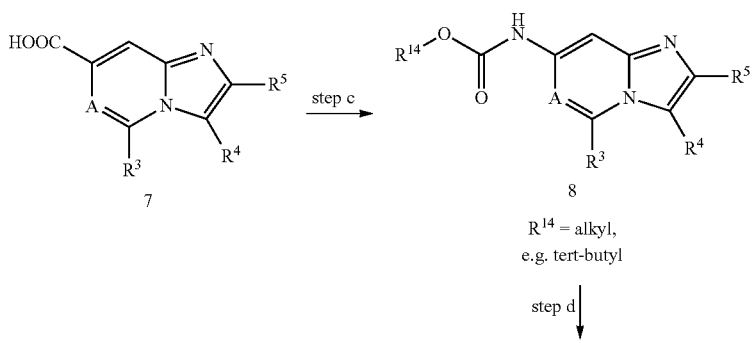

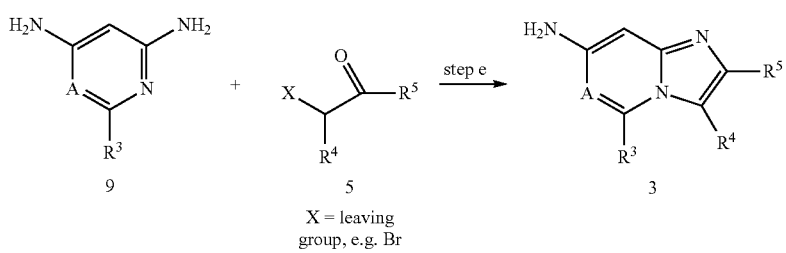

Compounds of formula 2 with $R^2$=COOEt can be prepared according to Scheme 3, in close analogy to known procedures: Compound 10 is reacted with a hydrazine, or a salt thereof, to give a pyrazole 12 (step f, similar to the method of A. Hanzlowsky, B. Jelencic, S. Recnik, J. Svete, A. Golobic, B. Stanovnik *J. Heterocyclic Chem.* 2003, 40(3), 487-498). Selective mono-saponification of diester 12 then yields 2-COOEt (step g, similar to the method of Pérez et al., Spanish patent appl. ES 493459).

Scheme 3

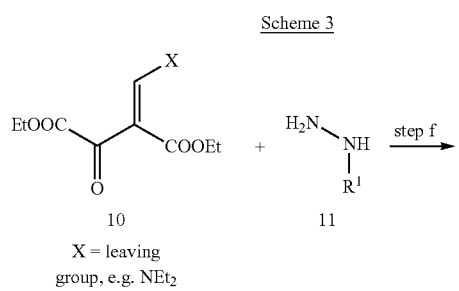

X = leaving group, e.g. NEt$_2$

Scheme 4

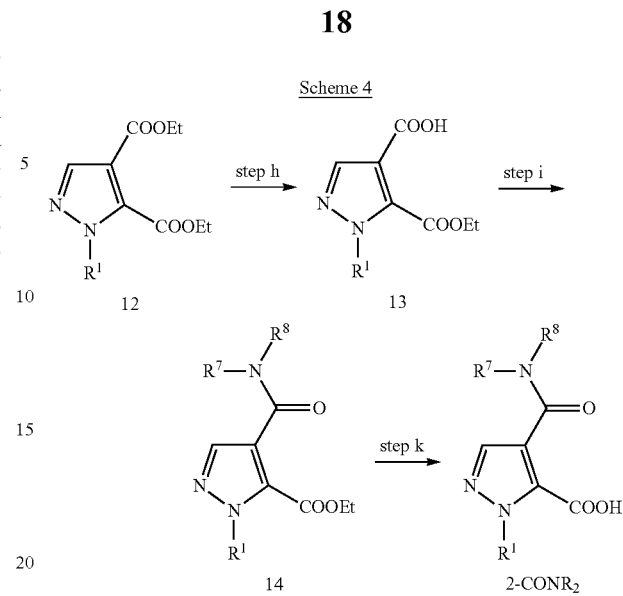

Compounds of formula 1 can be further transformed according to Scheme 5. For instance, 1-COOEt can be saponified, e.g. by reaction with KOH, to give 15 (step l). Upon activation with a suitable reagent such as TBTU, acid 15 can be converted with a primary or secondary amine to 1-CONR$_2$ (step m). Alternatively, 1-COOEt can be directly converted into 1-CONR$_2$, e.g. by reaction with an amine such as methylamine (step n).

Scheme 5

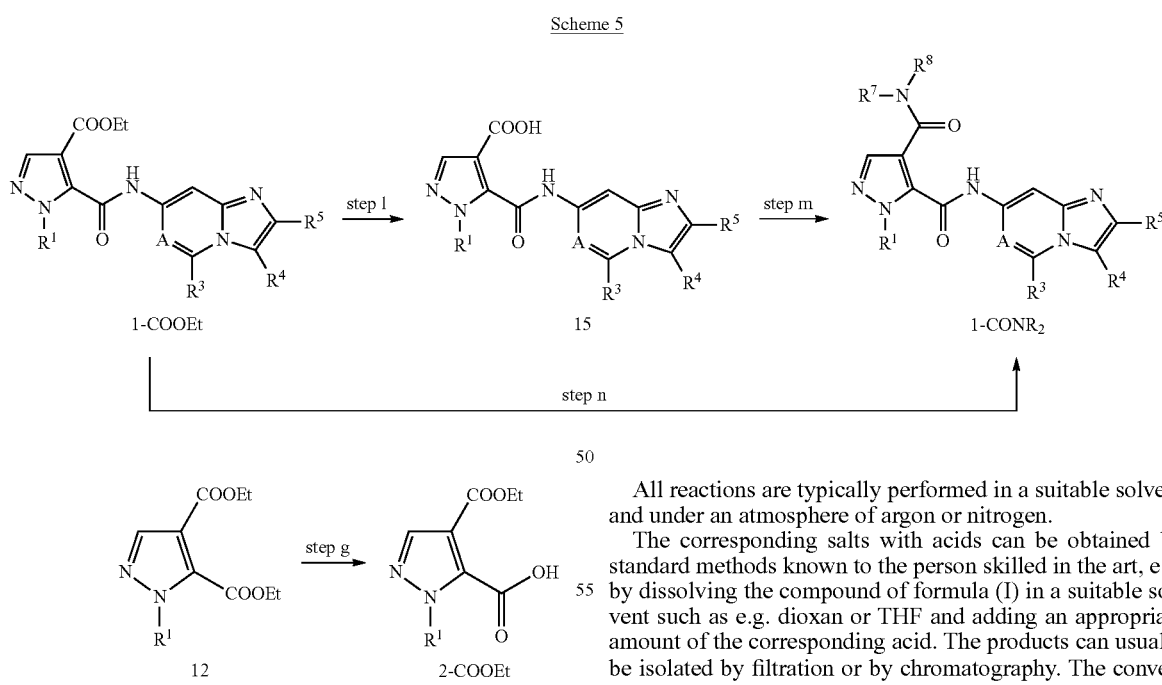

Compounds of formula 2 with $R^2$=CONR$^7$R$^8$ can be prepared according to Scheme 4: Diester 12 can be selectively mono-saponified to 13 by a suitable biochemical (enzymatic) transformation (step h). The obtained acid is then activated, e.g. with a coupling reagent such as propylphosphonic anhydride, and reacted with a primary or secondary amine to give amide 14 (step i). 14 can be saponified, e.g. by reaction with NaOH, to give 2-CONR$_2$ (step k).

All reactions are typically performed in a suitable solvent and under an atmosphere of argon or nitrogen.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or 0-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore provides pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by PDE10A inhibitors, particularly as therapeutically active substances for the treatment and/or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

In another embodiment, the invention provides a method for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, which method comprises administering a compound as defined above to a human being or animal.

The invention also embraces the use of compounds as defined above for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

The invention also relates to the use of compounds as described above for the preparation of medicaments for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer. Such medicaments comprise a compound as described above.

Prevention and/or treatment of schizophrenia is a preferred indication. Furthermore, prevention and/or treatment of positive, negative and/or cognitive symptoms associated with schizophrenia is preferred.

The following tests were carried out in order to determine the activity of the compounds of the present invention. PDE10 activity of the compounds of the present invention is determined using a Scintillation Proximity Assay (SPA)- based method similar to the one previously described (Fawcett, L. et al., Proc Natl Acad Sci USA (2000) 97(7):3702-3707). PDE10A1 and PDE10A2 are two splice variants of PDE10A. There are these 2 splice variants known, which differ in the N-terminal part of the protein. The catalytic domains of PDE10A1 and PDE10A2 are identical. The assay for PDE10A2 described below is therefore also representative for PDE10A1 and also for PDE10A in general.

The PDE10A2 assay was performed in a two step procedure in 96-well micro titer plates. The reaction mixture of 80 µl contained 20 mM HEPES/10 mM $MgCl_2$/0.05 mg/ml buffer (pH 7.5), 50 nM cGMP (Sigma) and 50 nM [$^3$H]-cGMP (GE Healthcare), 0.25 nM PDE10A2 with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A2 activity 50%). Non-specific activity was tested without the enzyme. The reaction was initiated by addition of the substrate solution (cGMP and [$^3$H]-cGMP) and allowed to progress for 30 minutes at room temperature. The reaction was terminated by transferring 50 µl of the reaction mixture into an OptiPlate (Perkin Elmer) containing 25 µl of YSi-SPA scintillation beads (GE Healthcare) in 18 mM zinc sulphate solution (stop reagent). After 1 h under shaking, the plate was centrifuged one minute at 1000 rpm to allow beads to settle. Afterwards, radioactive counts were measured on a Perkin Elmer TopCount Scintillation plate reader.

The catalytic domain of human PDE10A2, residues serine 449 to aspartate 789, was amplified by PCR using cDNA (Origene) and the oligonucleotides 5'-GGGGACAAG-TTTGTACAAAAAAGCAGGC*TTA*GTACCTAGAGGAT-CAAGCATTTGTAC TTCAGAAG-3' (Seq. ID no. 1) (with AttB1 recombination site in bold and thrombin protease cleavage site in italics) and 5'-GGGGACCACTTTGTACAA-GAAAGCTGGGTCAATCTTCAGATGCAGCTG-3' (Seq. ID no. 2) (with AttB2 recombination site in bold) which conferred Gateway recombination sites. The PCR product was used in a BP recombination reaction with pDONR221 to generate pENTR Thm-PDE10A2(S449-D789) which was DNA sequence verified and then used in an LR recombination reaction with a Gateway modified version of pET11a. The resulting expression vector, placT7.2 H6-(gwl)-Thm-PDE10A2(S449-D789) was DNA sequence confirmed and transformed into *E. coli* strain BL21(DE3) pLysS and recombinant protein was produced in TB medium at 20° C. by induction to a final IPTG concentration of 0.5 mM at an optical density of 1.0 at 600 nm for 20 hours. About 30% of the protein was in the soluble fraction of the cell homogenate. The protein was purified using sequential chromatography on Ni-NTA and HiTrapQ/HiTrapS. After thrombin digest at room temperature a HiTrapChelating/HiTrap Benzamindin chromatography removed impurities, uncleaved protein and thrombin. Final purification of PDE10A2(S449-D789) was performed on a Superdex 75 size exclusion chromatography equilibrated with 25 mM HEPES pH 8.4, 0.15 M NaCl. The yield of pure protein was 2 mg/liter of culture volume is relatively low. The purity of the protein was >95%, monomeric and monodisperse as shown by SDS-PAGE, HPLC and analytical ultracentrifugation.

The compounds according to formula (I) preferably have an $IC_{50}$ value below 10 µM, preferably below 5 µM, more preferably below 1 µM. Preferably, the $IC_{50}$ values are above 0.01 nM. The following table shows data for some examples.

| Example | PDE10A2 inhibition $IC_{50}$ [µmol/l] |
|---|---|
| 1 | 0.0252 |
| 2 | 0.0039 |
| 3 | 0.0002 |
| 5 | 0.0450 |
| 10 | 0.0027 |
| 11 | 0.0107 |
| 14 | 0.0022 |
| 17 | 0.0003 |
| 19 | 0.0010 |
| 20 | 0.0001 |
| 21 | 0.0021 |
| 24 | 0.0023 |
| 26 | <0.0001 |
| 27 | 0.0115 |
| 28 | 0.0007 |
| 29 | 0.0018 |
| 33 | 0.0023 |
| 35 | 0.0009 |
| 36 | 0.0019 |
| 37 | 0.0035 |
| 39 | 0.0033 |
| 41 | 0.0018 |
| 43 | 0.0031 |
| 46 | 0.0010 |
| 48 | 0.0008 |
| 50 | 0.0003 |
| 52 | 0.0047 |
| 53 | 0.0033 |
| 55 | 0.0043 |
| 59 | 0.0006 |
| 62 | 0.0126 |
| 65 | 0.0418 |
| 66 | 0.0020 |
| 67 | 0.0001 |
| 69 | 0.0010 |
| 70 | 0.0003 |
| 72 | 0.0008 |
| 74 | 0.0007 |
| 75 | 0.0010 |
| 80 | 0.0070 |
| 82 | 0.0001 |
| 84 | 0.0027 |
| 85 | 0.0006 |
| 86 | 0.0003 |
| 89 | 0.0001 |

The invention provides pharmaceutical compositions which comprise compounds of formula I and/or their pharmaceutically acceptable salts and a pharmaceutical carrier. The compositions can be, for example, in a form suitable for enteral, parenteral or topical administration. They can be administered, for example, perorally, e.g. in the form of tablets, coated tablets, dragés, hard and soft gelatin capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragés and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage at which compounds of formula I can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 0.1-500 mg, preferably 1-200 mg, of a compound of formula I.

The following examples serve to illustrate the present invention in more detail. They are, however, not intended to limit its scope in any manner.

EXAMPLES

Example 1

4-Chloro-2-methyl-2H-pyrazole-3-carboxylic acid (2-phenyl-imidazo[1,2-a]pyridin-7-yl)-amide

Step 1:
2-Phenyl-imidazo[1,2-a]pyridine-7-carboxylic acid methyl ester

A mixture of 2-amino-isonicotinic acid methyl ester (5 g, 32 mmol), w-bromoacetophenone (6.47 g, 32 mmol), NaHCO$_3$ (2.95 g, 35 mmol) and methanol (30 ml) was heated under an atmosphere of argon to reflux (3 h). After cooling, water (20 ml) was added, the mixture was stirred at r.t. (15 min), and filtered. The obtained solid was washed (water, methanol, diethyl ether) and dried under vacuum. The product (6.8 g, 85%) was used in the next step without further purification. MS (m/e)=253.2 [M+H$^+$].

Step 2:
2-Phenyl-imidazo[1,2-a]pyridine-7-carboxylic acid

A solution of NaOH in water (1N, 54 ml, 54 mmol) was added to a suspension of 2-phenyl-imidazo[1,2-a]pyridine-7-carboxylic acid methyl ester (6.8 g, 27 mmol) in a mixture of ethanol (50 ml) and water (25 ml). The mixture was heated to reflux (2 h). The obtained clear solution was cooled, poured onto crushed ice (50 g); HCl (25%, 10 ml) was added. The mixture was then filtered, and the precipitate was washed (ethanol) and dried under vacuum. The obtained solid (6.36 g, 99%) was used in the next step without further purification. MS (m/e)=239.1 [M+H$^+$].

Step 3:
(2-Phenyl-imidazo[1,2-a]pyridin-7-yl)-carbamic acid tert-butyl ester

Under an atmosphere of argon, diphenylphosphoryl azide (8.16 g, 27 mmol) was added to a solution of 2-phenyl-imidazo[1,2-a]pyridine-7-carboxylic acid (6.36 g, 27 mmol) and triethylamine (5.40 g, 53 mmol) in tert-butanol (100 ml). The mixture was heated to reflux overnight, then cooled and diluted with ethyl acetate (100 ml). The mixture was filtered, and the filtrate was washed (NH$_4$Cl satd., water, brine), and dried (Na$_2$SO$_4$). The title compound (4.81 g, 55%) was isolated from the residue by column chromatography (silica gel, CH$_2$Cl$_2$: MeOH=100:0-60:40). MS (m/e)=254.2 [M-Boc+H$^+$].

Step 4: 2-Phenyl-imidazo[1,2-a]pyridin-7-ylamine

Trifluoroacetic acid (30 ml) was added to a solution of (2-phenyl-imidazo[1,2-a]pyridin-7-yl)-carbamic acid tert-butyl ester (4.81 g, 15 mmol) in CH$_2$Cl$_2$ (30 ml), and the mixture was stirred at r.t. overnight. The mixture was then washed (water, 2×50 ml), dried (Na$_2$SO$_4$), and the solvent was evaporated. The title compound (2.25 g, 73%) was obtained from the residue by column chromatography (silica gel, CH$_2$Cl$_2$: MeOH=100:0-60:40). MS (m/e)=210.1 [M+H$^+$].

Step 5: 4-Chloro-2-methyl-2H-pyrazole-3-carboxylic acid (2-phenyl-imidazo[1,2-a]pyridin-7-yl)-amide Under an atmosphere of nitrogen, N—N-diisopropylethylamine (749 mg, 6 mmol) and 2-(1H-benzotriazole-1-yl)-1,1,3,3-tetramethyluronium tetrafluoroborate (TBTU, 744 mg, 1.94 mmol) were added to a solution of 4-chloro-2-methyl-2H-pyrazole-3-carboxylic acid (310 mg, 1.94 mmol, Art-Chem B000148) in DMF (5 ml). After 30 min, 2-phenyl-imidazo[1,2-a]pyridin-7-ylamine (404 mg, 1.94 mmol) was added, and the brown solution was stirred over the weekend (r.t.). The reaction mixture was taken up in ethyl acetate and washed with water. After drying (Na$_2$SO$_4$), the solvent was evaporated and the title compound (170 mg, 25%) was isolated by column chromatography (silica gel, heptane:ethyl acetate=100:0-50:50). MS (m/e)=352.2 [M+H$^+$].

Example 2

2-Methyl-2H-pyrazole-3,4-dicarboxylic acid 4-amide 3-[(2-phenyl-imidazo[1,2-a]pyridin-7-yl)-amide]

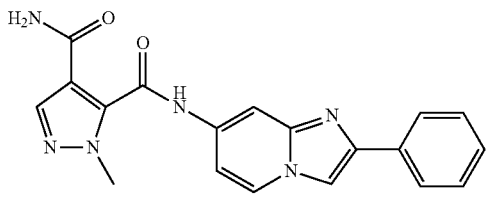

The title compound was prepared in analogy to Example 1, using 4-carbamoyl-2-methyl-2H-pyrazole-3-carboxylic acid (Art-Chem, B025769) in step 5. MS (m/e)=361.2 [M+H$^+$].

Example 3

2-Methyl-2H-pyrazole-3,4-dicarboxylic acid 4-dimethylamide 3-[(2-phenyl-imidazo[1,2-a]pyridin-7-yl)-amide]

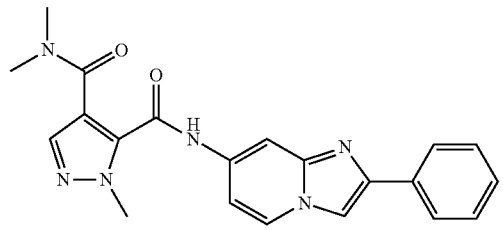

The title compound was prepared in analogy to Example 1, using 4-dimethylcarbamoyl-2-methyl-2H-pyrazole-3-carboxylic acid (Art-Chem, B026646) in step 5. MS (m/e)=389.3 [M+H$^+$].

Example 4

2-Methyl-2H-pyrazole-3,4-dicarboxylic acid 4-dimethylamide 3-{[2-(4-fluoro-phenyl)-imidazo[1,2-a]pyridin-7-yl]-amide}

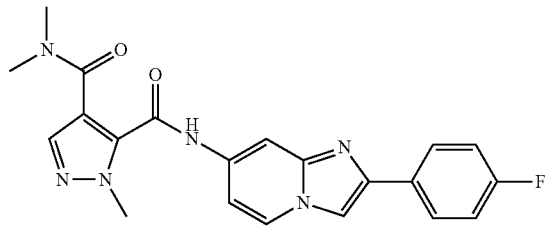

The title compound was prepared in analogy to Example 1, using 4-fluorophenacyl bromide in step 1, and 4-dimethylcarbamoyl-2-methyl-2H-pyrazole-3-carboxylic acid (Art-Chem, B026646) in step 5. MS (m/e)=407.2 [M+H$^+$].

Example 5

4-Chloro-2-methyl-2H-pyrazole-3-carboxylic acid (2-thiazol-2-yl-imidazo[1,2-a]pyridin-7-yl)-amide

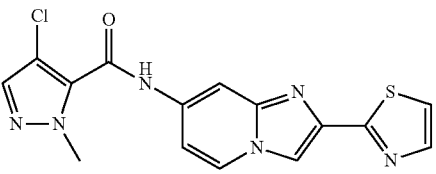

The title compound was prepared in analogy to Example 1, using 2-bromo-1-thiazol-2-yl-ethanone in step 1. MS (m/e)=359.0 [M+H$^+$].

Example 6

2-Methyl-2H-pyrazole-3,4-dicarboxylic acid 4-methylamide 3-[(2-phenyl-imidazo[1,2-a]pyridin-7-yl)-amide]

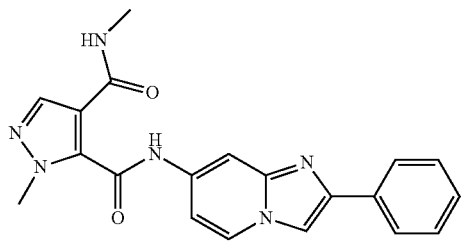

Methylamine (2N in methanol, 2 ml) was added to a solution of 1-methyl-5-(2-phenyl-imidazo[1,2-a]pyridin-7-ylcarbamoyl)-1H-pyrazole-4-carboxylic acid ethyl ester (Example 10, 100 mg, 0.26 mmol) in THF (2 ml). The light brown suspension was kept for 3 days at r.t. The solvent was then evaporated and the title compound (46 mg, 49%) was isolated from the residue by preparative, inverse-phase HPLC (Agilent Zorbax XdB-C18 column, time per run ~7 min, flow rate 30 ml/min, solvent gradient H$_2$O/CH$_3$CN=95:5-5:95). MS (m/e)=375.2 [M+H$^+$].

Example 7

2-Methyl-2H-pyrazole-3,4-dicarboxylic acid 4-dimethylamide 3-{[2-(3-fluoro-phenyl)-imidazo[1,2-a]pyridin-7-yl]-amide}

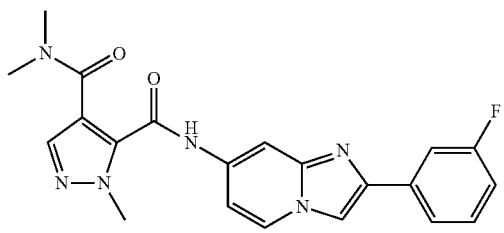

The title compound was prepared in analogy to Example 1, using 3-fluorophenacyl bromide in step 1, and 4-dimethylcarbamoyl-2-methyl-2H-pyrazole-3-carboxylic acid (Art-Chem, B026646) in step 5. MS (m/e)=407.2 [M+H⁺].

Example 8

2-Methyl-2H-pyrazole-3,4-dicarboxylic acid 4-dimethylamide 3-[(2-thiazol-2-yl-imidazo[1,2-a]pyridin-7-yl)-amide]

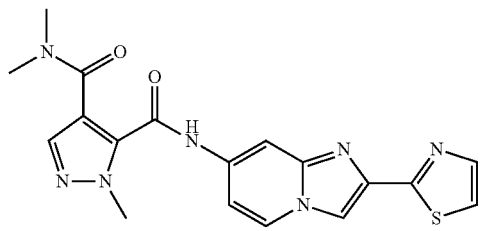

The title compound was prepared in analogy to Example 1, using 2-bromo-1-thiazol-2-yl-ethanone in step 1, and 4-dimethylcarbamoyl-2-methyl-2H-pyrazole-3-carboxylic acid (Art-Chem, B026646) in step 5. MS (m/e)=396.1 [M+H⁺].

Example 9

4-Chloro-2-methyl-2H-pyrazole-3-carboxylic acid (3-methyl-2-phenyl-imidazo[1,2-a]pyridin-7-yl)-amide

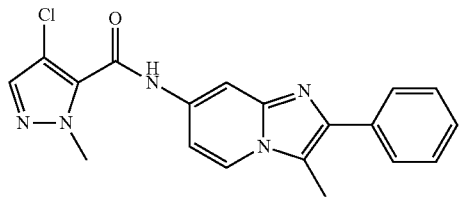

The title compound was prepared in analogy to Example 1, using α-bromopropiophenone in step 1. MS (m/e)=366.1 [M+H⁺].

Example 10

1-Methyl-5-(2-phenyl-imidazo[1,2-a]pyridin-7-ylcarbamoyl)-1H-pyrazole-4-carboxylic acid ethyl ester

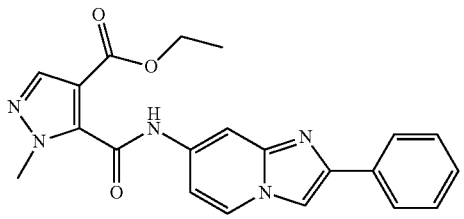

Step 1: 2-Methyl-2H-pyrazole-3,4-dicarboxylic acid diethyl ester

Under an atmosphere of argon, methylhydrazine (1.15 g, 25 mmol) and HCl (36.5% in water, 2.5 ml) were added to a solution of 2-dimethylaminomethylene-3-oxo-succinic acid diethyl ester (6.07 g, 25 mmol, obtained by the method of Hanzlowsky et al., *J. Heterocyclic Chem.* 2003, 40(3), 487-498) in ethanol (200 ml). The mixture was heated to 60° C. until HPLC analysis indicated the disappearance of the starting material (2 h). The solvent was evaporated, and the residue was taken up in dichloromethane and washed (water). The organic layer was dried (Na₂SO₄), the solvent was evaporated and the title compound (2.06 mg, 36%) was isolated from the mixture by column chromatography (silica gel, heptane:ethyl acetate=100:0-60:40). (The regioisomeric 1-methyl-1H-pyrazole-3,4-dicarboxylic acid diethyl ester can also be isolated, and can be distinguished from the desired product by NOE-¹H-NMR.) MS (m/e)=227.2 [M+H⁺].

Step 2: 2-Methyl-2H-pyrazole-3,4-dicarboxylic acid 4-ethyl ester (This compound was prepared in close analogy to the method of Perez et al., Spanish patent appl. ES 493459.) 2-Methyl-2H-pyrazole-3,4-dicarboxylic acid diethyl ester (2.06 g, 9.1 mmol) was suspended in a NaOH solution (0.5M in water, 20 ml, 10 mmol) and heated to reflux (30 min). If the conversion was incomplete after this time, as indicated by HPLC control, small amounts of NaOH were added in 30 min intervals. The reaction mixture was cooled, and HCl was added, and stirred for an additional 30 min (r.t.). The precipitate was filtered, washed (water, small amount) and dried under vacuum. The title compound was obtained as a white solid (1.27 g, 70%), and was used in the next step without further purification. MS (m/e)=198 [M+H⁺].

Step 3: 1-Methyl-5-(2-phenyl-imidazo[1,2-a]pyridin-7-ylcarbamoyl)-1H-pyrazole-4-carboxylic acid ethyl ester The title compound was prepared in analogy to Example 1, using 2-methyl-2H-pyrazole-3,4-dicarboxylic acid 4-ethyl ester in step 5. MS (m/e)=390.3 [M+H⁺].

Example 11

5-(2-Phenyl-imidazo[1,2-a]pyridin-7-ylcarbamoyl)-1H-pyrazole-4-carboxylic acid ethyl ester

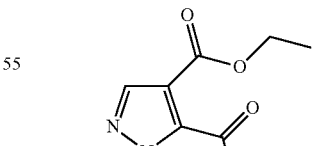

The title compound was prepared in analogy to Example 10, using hydrazine monohydrate hydrochloride in step 1. MS (m/e)=376.4 [M+H⁺].

Example 12

1-Ethyl-5-(2-phenyl-imidazo[1,2-a]pyridin-7-ylcarbamoyl)-1H-pyrazole-4-carboxylic acid ethyl ester

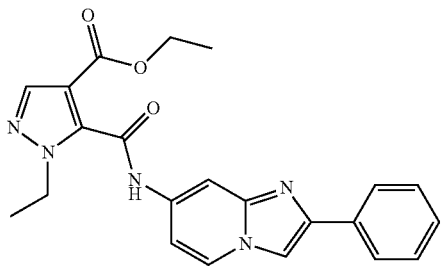

Step 1: 2H-Pyrazole-3,4-dicarboxylic acid diethyl ester

Under an atmosphere of argon, hydrazine monohydrate hydrochloride (1.91 g, 28 mmol) and HCl (36.5% in water, 2.8 ml) were added to a solution of 2-dimethylaminomethylene-3-oxo-succinic acid diethyl ester (6.8 g, 28 mmol, obtained by the method of Hanzlowsky et al., *J. Heterocyclic Chem.* 2003, 40(3), 487-498) in ethanol (100 ml). The mixture was heated to 60° C. (3 h). The solvent was evaporated, and the residue was taken up in dichloromethane and washed (water). The organic layer was dried ($Na_2SO_4$), the solvent was evaporated and the title compound (1.81 mg, 31%) was isolated from the mixture by column chromatography (silica gel, heptane:ethyl acetate=100:0-60:40). MS (m/e)=383.3 $[M+H^+]$.

Step 2: 2-Ethyl-2H-pyrazole-3,4-dicarboxylic acid diethyl ester

Sodium ethanolate solution was freshly prepared by dissolving sodium (240 mg) in ethanol (30 ml). 2H-Pyrazole-3,4-dicarboxylic acid diethyl ester (800 mg, 3.77 mmol) was dissolved in this sodium ethanolate solution (11 ml) and stirred for 10 min (r.t.), before ethyl iodide (1.4 g, 9 mmol) was added dropwise. After the completion of the addition, the mixture was heated to reflux until all starting material was consumed (1 h). The solvent was then evaporated, the residue was taken up in ethyl acetate and washed (water). The organic layer was dried ($Na_2SO_4$), evaporated, and the title compound (280 mg, 31%) was isolated from the mixture by column chromatography (silica gel, heptane:ethyl acetate=100:0-60:40). (The regioisomeric 1-ethyl-1H-pyrazole-3,4-dicarboxylic acid diethyl ester can also be isolated, and can be distinguished from the desired product by NOE-$^1$H-NMR.) MS (m/e)=241.1 $[M+H^+]$.

Step 3: 2-Ethyl-2H-pyrazole-3,4-dicarboxylic acid 4-ethyl ester

2-Ethyl-2H-pyrazole-3,4-dicarboxylic acid diethyl ester (280 mg, 1.2 mmol) was suspended in a NaOH solution (0.5M in water, 2.8 ml) and stirred at r.t. until HPLC analysis indicated the consumption of the starting material (4 h). HCl (1N, 1 ml) was added, and the mixture was extracted with ethyl acetate. The combined organic layers were dried ($Na_2SO_4$), evaporated, and the title compound (200 mg, 81%) was isolated from the mixture by column chromatography (silica gel, heptane:ethyl acetate=100:0-60:40). MS (m/e)= 211.1 $[M-H^+]$.

Step 4: 1-Ethyl-5-(2-phenyl-imidazo[1,2-a]pyridin-7-ylcarbamoyl)-1H-pyrazole-4-carboxylic acid ethyl ester The title compound was prepared in analogy to Example 1, using 2-ethyl-2H-pyrazole-3,4-dicarboxylic acid 4-ethyl ester in step 5. MS (m/e)=404.4 $[M+H^+]$.

Example 13

2-Methyl-4-(pyrrolidine-1-carbonyl)-2H-pyrazole-3-carboxylic acid (2-phenyl-imidazo[1,2-a]pyridin-7-yl)-amide

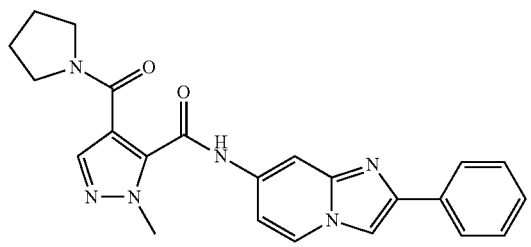

Step 1: 1-Methyl-5-(2-phenyl-imidazo[1,2-a]pyridin-7-ylcarbamoyl)-1H-pyrazole-4-carboxylic acid KOH (1.67 g, 26 mmol) was added to a solution of 1-methyl-5-(2-phenyl-imidazo[1,2-a]pyridin-7-ylcarbamoyl)-1H-pyrazole-4-carboxylic acid ethyl ester (Example 10, 6.65 g, 17 mmol) in ethanol (150 ml) and the mixture was heated to reflux (4 h). The solvent was evaporated and water and ethanol (as little as needed to avoid sticky precipitate) was added. HCl (conc., 12 ml) was added, the white suspension was stirred for 30 min (r.t.) and filtered. The precipitated title compound (7.19 g, 99%) was isolated and dried under vacuum. MS (m/e)=362.2 $[M+H^+]$.

Step 2: 2-Methyl-4-(pyrrolidine-1-carbonyl)-2H-pyrazole-3-carboxylic acid (2-phenyl-imidazo[1,2-a]pyridin-7-yl)-amide TBTU (75 mg) and diisopropylethylamine (75 mg) were added to a solution of 1-methyl-5-(2-phenyl-imidazo[1,2-a]pyridin-7-ylcarbamoyl)-1H-pyrazole-4-carboxylic acid (70 mg) in DMF (2 ml), and the mixture was stirred at r.t. (30 min). Pyrrolidine (14 mg) was added to the brown solution, and the reaction mixture was stirred at r.t. overnight. Water was added and the mixture was extracted several times with ethyl acetate. The combined organic layers were dried ($Na_2SO_4$), and evaporated. The title compound (43 mg, 54%) was isolated from the residue by preparative, inverse-phase HPLC (Agilent Zorbax XdB-C18 column, time per run ~7 min, flow rate 30 ml/min, solvent gradient $H_2O/CH_3CN$=95:5-5:95). MS (m/e)=415.3 $[M+H^+]$.

Example 14

5-(6-Cyano-2-phenyl-imidazo[1,2-a]pyridin-7-ylcarbamoyl)-1-methyl-1H-pyrazole-4-carboxylic acid ethyl ester

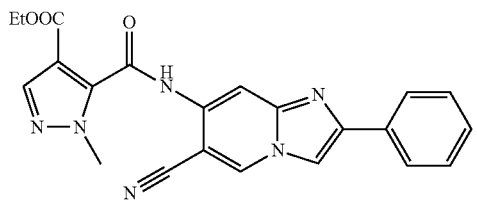

Step 1: 7-Amino-2-phenyl-imidazo[1,2-a]pyridine-6-carbonitrile

2-Bromoacetophenone (1.11 g, 5.6 mmol) and NaHCO₃ (470 mg) were added to a solution of 3-cyano-4,6-diaminopyridine (500 mg, 3.7 mmol) in methanol (7.5 ml), and the mixture was heated to reflux overnight. The mixture was cooled, water (4 ml) was added, and the precipitate was filtered to give a first crop of the desired product. The filtrate was evaporated, taken up in ethyl acetate and washed (water, brine). The organic layer was dried (Na₂SO₄), evaporated, and the residue was purified by column chromatography (silica gel, heptane:ethyl acetate=100:0-60:40) to yield a second crop of product. The combined isolates were dried to give the title compound (350 mg, 40%). MS (m/e)=235.1 [M+H$^+$].

Step 2: 5-Chlorocarbonyl-1-methyl-1H-pyrazole-4-carboxylic acid ethyl ester

A mixture of 2-ethyl-2H-pyrazole-3,4-dicarboxylic acid 4-ethyl ester (Example 10, steps 1-3, 3 g, 15 mmol) and thionyl chloride (40 ml) was heated to reflux (4 h). The thionyl chloride was evaporated, and the residue (3.38 g, 64%) was used in the next step without further purification.

Step 3: 5-(6-Cyano-2-phenyl-imidazo[1,2-a]pyridin-7-ylcarbamoyl)-1-methyl-1H-pyrazole-4-carboxylic acid ethyl ester 5-Chlorocarbonyl-1-methyl-1H-pyrazole-4-carboxylic acid ethyl ester (940 mg, 4.33 mmol) was added slowly to a solution of 7-amino-2-phenyl-imidazo[1,2-a]pyridine-6-carbonitrile (410 mg, 1.8 mmol) and triethylamine (363 mg) in dichloromethane (8 ml), and the mixture was stirred at r.t. overnight. The mixture was extracted with dichloromethane, the combined organic layers were dried (Na₂SO₄), and evaporated. The title compound (310 mg, 42%) was obtained by column chromatography (silica gel, heptane:ethyl acetate=80:20-60:40). MS (m/e)=413.3 [M−H$^+$].

Example 15

2-Methyl-2H-pyrazole-3,4-dicarboxylic acid 4-(methyl-propyl-amide) 3-[(2-phenyl-imidazo[1,2-a]pyridin-7-yl)-amide]

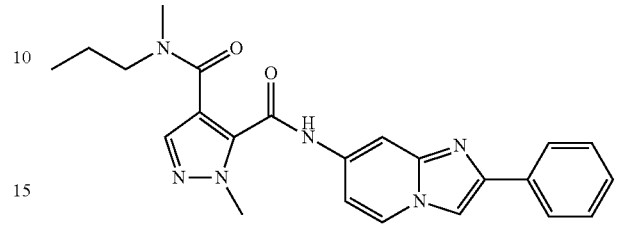

The title compound was prepared in analogy to Example 13, using N-methyl-N-propylamine in step 2. MS (m/e)=417.3 [M+H$^+$].

Example 16

2-Methyl-2H-pyrazole-3,4-dicarboxylic acid 4-[(2-methoxy-ethyl)-methyl-amide] 3-[(2-phenyl-imidazo[1,2-a]pyridin-7-yl)-amide]

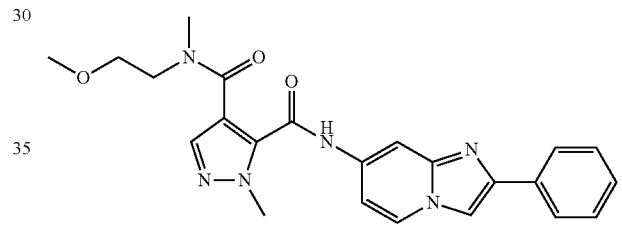

The title compound was prepared in analogy to Example 13, using (2-methoxy-ethyl)-methyl-amine in step 2. MS (m/e)=433.3 [M+H$^+$].

Example 17

4-(3,3-Difluoro-azetidine-1-carbonyl)-2-methyl-2H-pyrazole-3-carboxylic acid (2-phenyl-imidazo[1,2-a]pyridin-7-yl)-amide

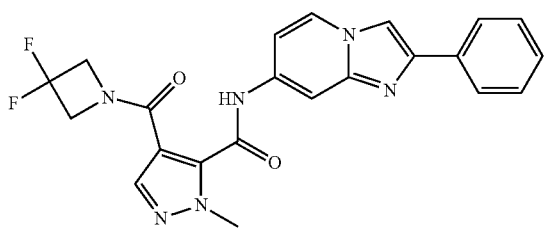

The title compound was prepared in analogy to Example 13, using 3,3-difluoro-azetidine in step 2. MS (m/e)=437.1 [M+H$^+$].

Example 18

2-Methyl-2H-pyrazole-3,4-dicarboxylic acid 3-[(2-phenyl-imidazo[1,2-a]pyridin-7-yl)-amide]-4-[(2,2,2-trifluoro-ethyl)-amide]

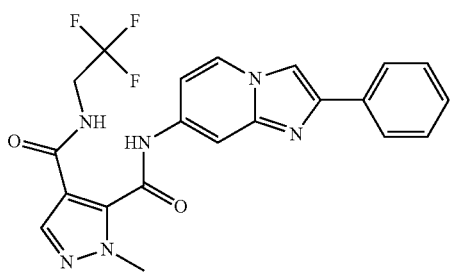

The title compound was prepared in analogy to Example 13, using 2,2,2-trifluoro-ethylamine in step 2. MS (m/e)=443.3 [M+H$^+$].

Example 19

2-Methyl-2H-pyrazole-3,4-dicarboxylic acid 4-cyclopropylamide 3-[(2-phenyl-imidazo[1,2-a]pyridin-7-yl)-amide]

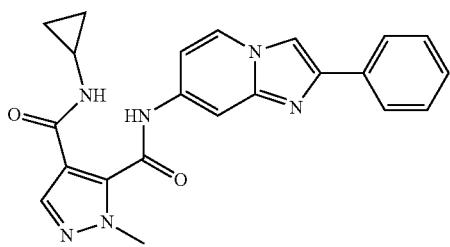

The title compound was prepared in analogy to Example 13, using cyclopropylamine in step 2. MS (m/e)=401.3 [M+H$^+$].

Example 20

2-Methyl-4-(morpholine-4-carbonyl)-2H-pyrazole-3-carboxylic acid (2-phenyl-imidazo[1,2-a]pyridin-7-yl)-amide

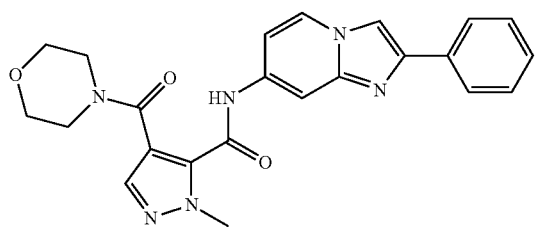

The title compound was prepared in analogy to Example 13, using morpholine in step 2. MS (m/e)=431.3 [M+H$^+$].

Example 21

2-Methyl-2H-pyrazole-3,4-dicarboxylic acid 4-[methyl-(2-methylamino-ethyl)-amide]3-[(2-phenyl-imidazo[1,2-a]pyridin-7-yl)-amide]

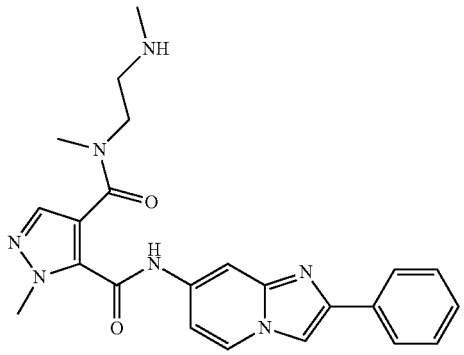

The title compound was prepared in analogy to Example 13, using N,N'-dimethyl-ethane-1,2-diamine in step 2. MS (m/e)=432.3 [M+H$^+$].

Example 22

2-Methyl-2H-pyrazole-3,4-dicarboxylic acid 4-diethylamide 3-[(2-phenyl-imidazo[1,2-a]pyridin-7-yl)-amide]

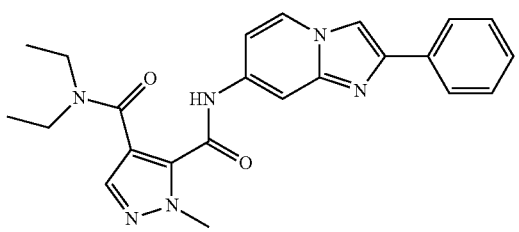

The title compound was prepared in analogy to Example 13, using diethyl-amine in step 2. MS (m/e)=417.3 [M+H$^+$].

Example 23

2-Methyl-2H-pyrazole-3,4-dicarboxylic acid 4-[(2-hydroxy-ethyl)-amide]3-[(2-phenyl-imidazo[1,2-a]pyridin-7-yl)-amide]

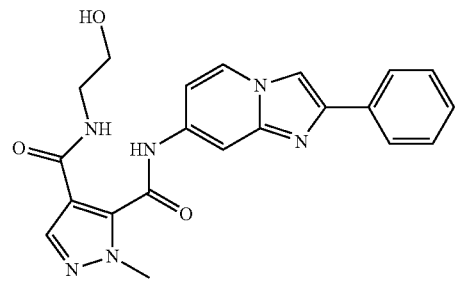

The title compound was prepared in analogy to Example 13, using 2-amino-ethanol in step 2. MS (m/e)=405.3 [M+H$^+$].

Example 24

2-Methyl-2H-pyrazole-3,4-dicarboxylic acid 4-tert-butylamide 3-[(2-phenyl-imidazo[1,2-a]pyridin-7-yl)-amide]

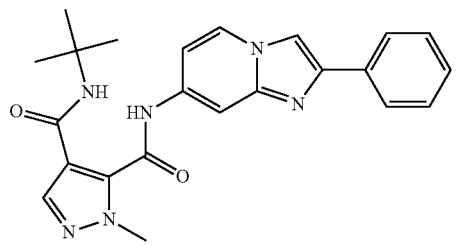

The title compound was prepared in analogy to Example 13, using tert-butylamine in step 2. MS (m/e)=417.3 [M+H$^+$].

Example 25

2-Methyl-2H-pyrazole-3,4-dicarboxylic acid 4-isopropylamide 3-[(2-phenyl-imidazo[1,2-a]pyridin-7-yl)-amide]

The title compound was prepared in analogy to Example 13, using isopropylamine in step 2. MS (m/e)=403.4 [M+H$^+$].

Example 26

4-(Azetidine-1-carbonyl)-2-methyl-2H-pyrazole-3-carboxylic acid (2-phenyl-imidazo[1,2-a]pyridin-7-yl)-amide

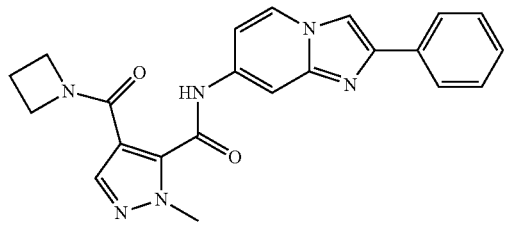

The title compound was prepared in analogy to Example 13, using azetidine in step 2. MS (m/e)=401.3 [M+H$^+$].

Example 27

4-(5,6-Dihydro-8H-[1,2,4]triazolo[4,3-a]pyrazine-7-carbonyl)-2-methyl-2H-pyrazole-3-carboxylic acid (2-phenyl-imidazo[1,2-a]pyridin-7-yl)-amide

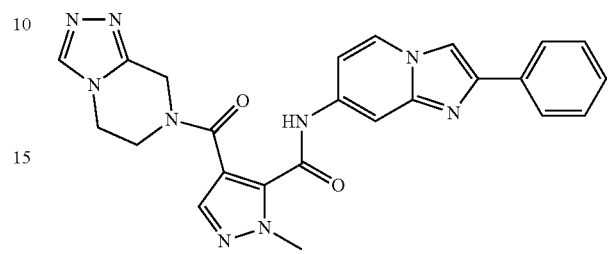

The title compound was prepared in analogy to Example 13, using 5,6,7,8-tetrahydro-[1,2,4]triazolo[4,3-a]pyrazine in step 2. MS (m/e)=468.3 [M+H$^+$].

Example 28

2-Methyl-2H-pyrazole-3,4-dicarboxylic acid 4-[(3-methoxy-propyl)-amide]3-[(2-phenyl-imidazo[1,2-a]pyridin-7-yl)-amide]

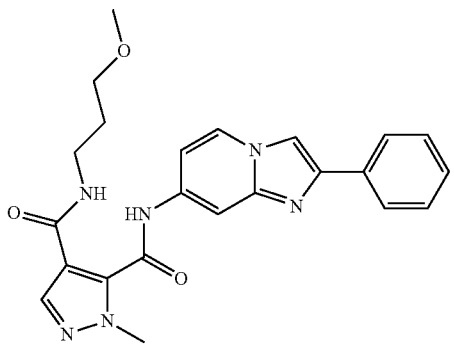

The title compound was prepared in analogy to Example 13, using 3-methoxy-propylamine in step 2. MS (m/e)=433.2 [M+H$^+$].

Example 29

2-Methyl-2H-pyrazole-3,4-dicarboxylic acid 4-[(3-hydroxy-propyl)-amide]3-[(2-phenyl-imidazo[1,2-a]pyridin-7-yl)-amide]

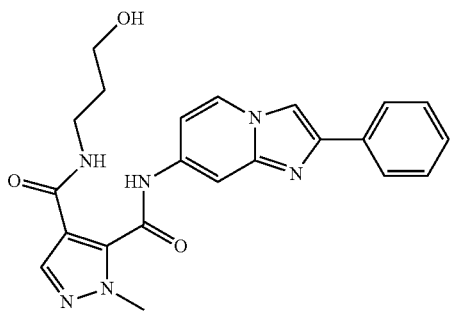

The title compound was prepared in analogy to Example 13, using 3-amino-propan-1-ol in step 2. MS (m/e)=419.1 [M+H$^+$].

Example 30

2-Methyl-2H-pyrazole-3,4-dicarboxylic acid 4-{[2-(2-hydroxy-ethoxy)-ethyl]-amide}3-[(2-phenyl-imidazo[1,2-a]pyridin-7-yl)-amide]

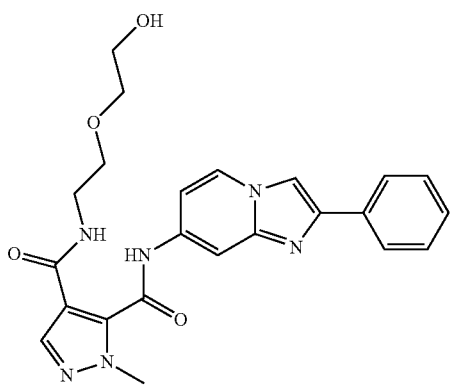

The title compound was prepared in analogy to Example 13, using 2-(2-amino-ethoxy)-ethanol in step 2. MS (m/e)= 449.2 [M+H$^+$].

Example 31

2-Methyl-2H-pyrazole-3,4-dicarboxylic acid 4-dimethylcarbamoylmethyl-amide 3-[(2-phenyl-imidazo[1,2-a]pyridin-7-yl)-amide]

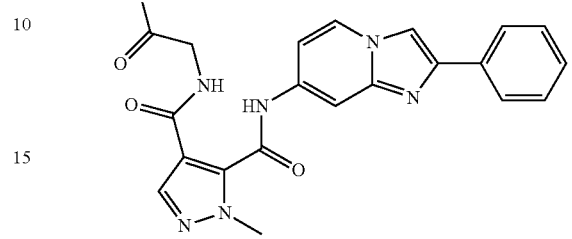

The title compound was prepared in analogy to Example 13, using 2-amino-N,N-dimethyl-acetamide in step 2. MS (m/e)=446.2 [M+H$^+$].

Example 32

2-Methyl-2H-pyrazole-3,4-dicarboxylic acid 4-(methoxy-methyl-amide) 3-[(2-phenyl-imidazo[1,2-a]pyridin-7-yl)-amide]

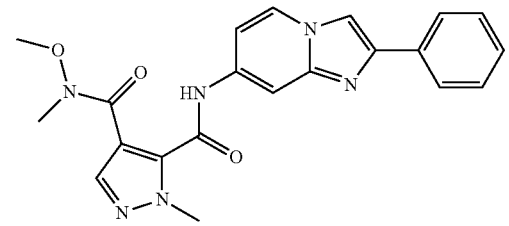

The title compound was prepared in analogy to Example 13, using O,N-dimethyl-hydroxylamine in step 2. MS (m/e)= 405.3 [M+H$^+$].

Example 33

2-Methyl-2H-pyrazole-3,4-dicarboxylic acid 4-[(3-hydroxymethyl-oxetan-3-ylmethyl)-amide]3-[(2-phenyl-imidazo[1,2-a]pyridin-7-yl)-amide]

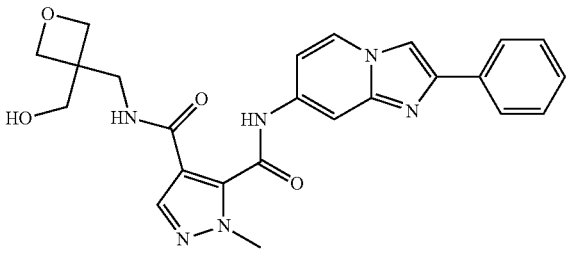

The title compound was prepared in analogy to Example 13, using (3-aminomethyl-oxetan-3-yl)-methanol in step 2. MS (m/e)=461.3 [M+H$^+$].

Example 34

2-Methyl-2H-pyrazole-3,4-dicarboxylic acid 4-[(2-oxo-tetrahydro-furan-3-yl)-amide]3-[(2-phenyl-imidazo[1,2-a]pyridin-7-yl)-amide]

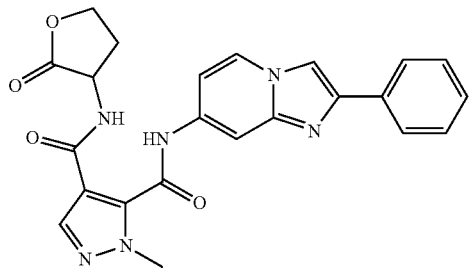

The title compound was prepared in analogy to Example 13, using 3-amino-dihydro-furan-2-one in step 2. MS (m/e)=445.2 [M+H$^+$].

Example 35

2-Methyl-2H-pyrazole-3,4-dicarboxylic acid 4-[(2-hydroxy-propyl)-amide]3-[(2-phenyl-imidazo[1,2-a]pyridin-7-yl)-amide]

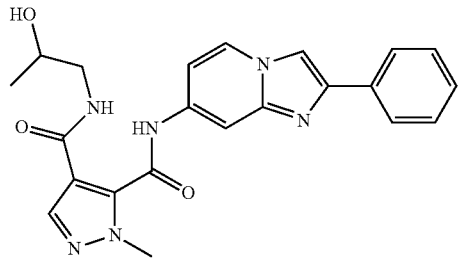

The title compound was prepared in analogy to Example 13, using 1-amino-propan-2-ol in step 2. MS (m/e)=419.2 [M+H$^+$].

Example 36

2-Methyl-2H-pyrazole-3,4-dicarboxylic acid 4-[(2-hydroxy-1-methyl-ethyl)-amide]3-[(2-phenyl-imidazo[1,2-a]pyridin-7-yl)-amide]

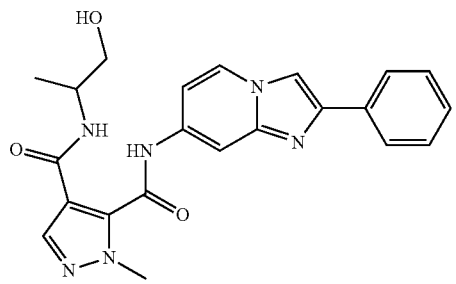

The title compound was prepared in analogy to Example 13, using 2-amino-propan-1-ol in step 2. MS (m/e)=419.2 [M+H$^+$].

Example 37

2-Methyl-2H-pyrazole-3,4-dicarboxylic acid 3-[(2-phenyl-imidazo[1,2-a]pyridin-7-yl)-amide]-4-[(tetrahydro-furan-2-ylmethyl)-amide]

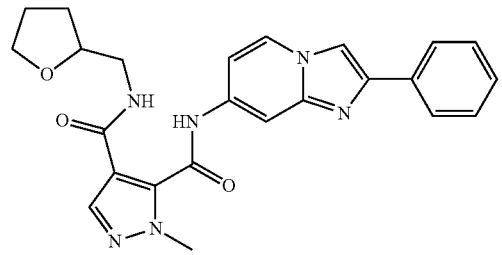

The title compound was prepared in analogy to Example 13, using C-(tetrahydro-furan-2-yl)-methylamine in step 2. MS (m/e)=445.3 [M+H$^+$].

Example 38

2-Methyl-4-(1-methyl-3,4-dihydro-1H-pyrrolo[1,2-a]pyrazine-2-carbonyl)-2H-pyrazole-3-carboxylic acid (2-phenyl-imidazo[1,2-a]pyridin-7-yl)-amide

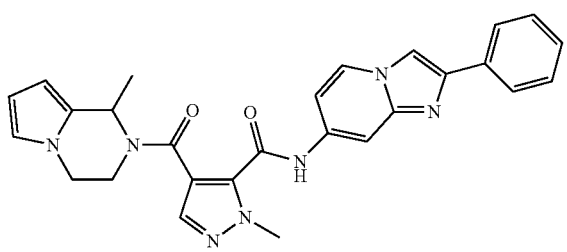

The title compound was prepared in analogy to Example 13, using 1-methyl-1,2,3,4-tetrahydro-pyrrolo[1,2-a]pyrazine in step 2. MS (m/e)=480.2 [M+H$^+$].

Example 39

2-Methyl-2H-pyrazole-3,4-dicarboxylic acid 3-[(2-phenyl-imidazo[1,2-a]pyridin-7-yl)-amide]-4-[(3,3,3-trifluoro-2-hydroxy-propyl)-amide]

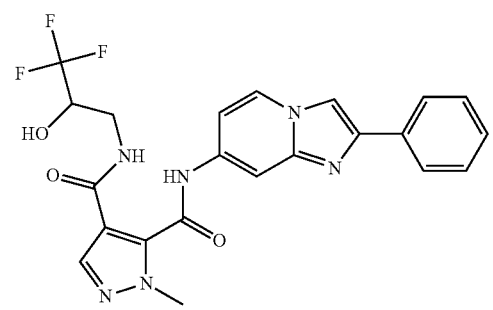

The title compound was prepared in analogy to Example 13, using 3-amino-1,1,1-trifluoro-propan-2-ol in step 2. MS (m/e)=473.1 [M+H$^+$].

Example 40

2-Methyl-2H-pyrazole-3,4-dicarboxylic acid 3-[(2-phenyl-imidazo[1,2-a]pyridin-7-yl)-amide]-4-[(tetrahydro-furan-3-ylmethyl)-amide]

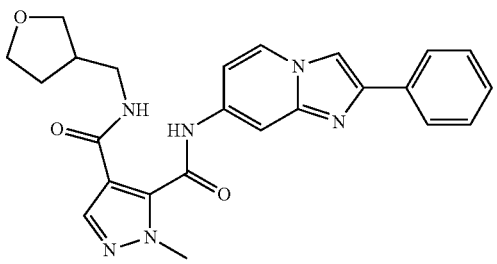

The title compound was prepared in analogy to Example 13, using C-(tetrahydro-furan-3-yl)-methylamine in step 2. MS (m/e)=445.3 [M+H$^+$].

Example 41

2-Methyl-2H-pyrazole-3,4-dicarboxylic acid 3-[(2-phenyl-imidazo[1,2-a]pyridin-7-yl)-amide]-4-[(tetrahydro-furan-3-yl)-amide]

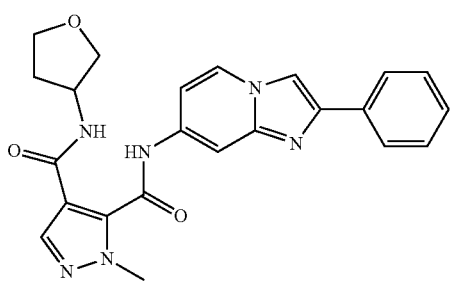

The title compound was prepared in analogy to Example 13, using tetrahydro-furan-3-ylamine in step 2. MS (m/e)=431.3 [M+H$^+$].

Example 42

2-Methyl-4-(2-oxa-6-aza-spiro[3.3]heptane-6-carbonyl)-2H-pyrazole-3-carboxylic acid (2-phenyl-imidazo[1,2-a]pyridin-7-yl)-amide

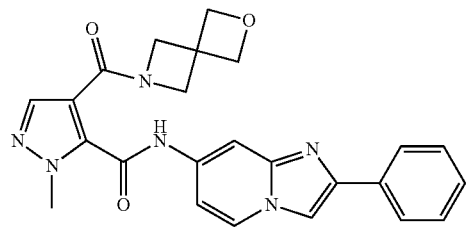

The title compound was prepared in analogy to Example 13, using 2-oxa-6-aza-spiro[3.3]heptane in step 2. MS (m/e)=443.3 [M+H$^+$].

Example 43

4-(5,6-Dihydro-8H-imidazo[1,2-a]pyrazine-7-carbonyl)-2-methyl-2H-pyrazole-3-carboxylic acid (2-phenyl-imidazo[1,2-a]pyridin-7-yl)-amide

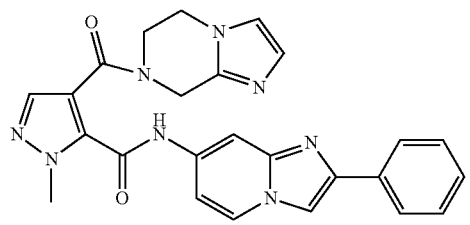

The title compound was prepared in analogy to Example 13, using 5,6,7,8-tetrahydro-imidazo[1,2-a]pyrazine in step 2. MS (m/e)=467.2 [M+H$^+$].

Example 44

2-Methyl-4-([1,4]oxazepane-4-carbonyl)-2H-pyrazole-3-carboxylic acid (2-phenyl-imidazo[1,2-a]pyridin-7-yl)-amide

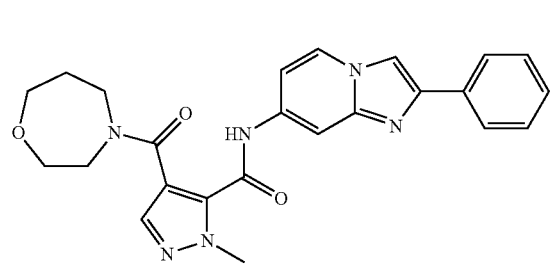

The title compound was prepared in analogy to Example 13, using [1,4]oxazepane in step 2. MS (m/e)=445.2 [M+H$^+$].

Example 45

4-(4-Acetyl-piperazine-1-carbonyl)-2-methyl-2H-pyrazole-3-carboxylic acid (2-phenyl-imidazo[1,2-a]pyridin-7-yl)-amide

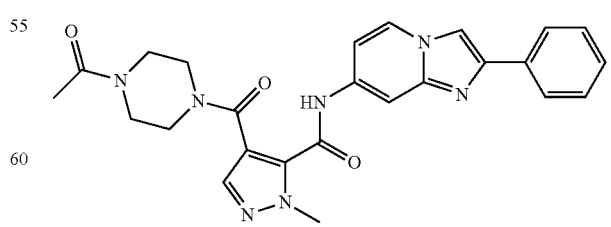

The title compound was prepared in analogy to Example 13, using 1-piperazin-1-yl-ethanone in step 2. MS (m/e)=472.2 [M+H$^+$].

Example 46

2-Methyl-4-(piperazine-1-carbonyl)-2H-pyrazole-3-carboxylic acid (2-phenyl-imidazo[1,2-a]pyridin-7-yl)-amide

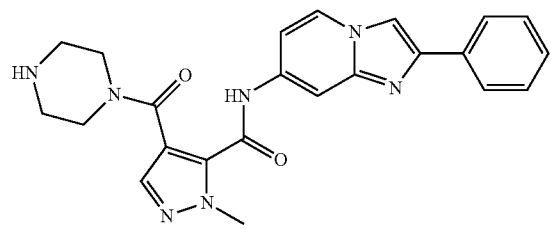

The title compound was prepared in analogy to Example 13, using piperazine in step 2. MS (m/e)=430.4 [M+H$^+$].

Example 47

4-((S)-2-Methoxymethyl-pyrrolidine-1-carbonyl)-2-methyl-2H-pyrazole-3-carboxylic acid (2-phenyl-imidazo[1,2-a]pyridin-7-yl)-amide

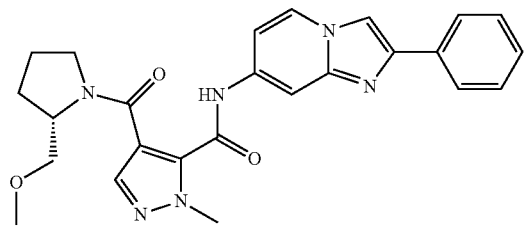

The title compound was prepared in analogy to Example 13, using (S)-2-Methoxymethyl-pyrrolidine in step 2. MS (m/e)=459.3 [M+H$^+$].

Example 48

4-(1,1-Dioxo-thiomorpholine-4-carbonyl)-2-methyl-2H-pyrazole-3-carboxylic acid (2-phenyl-imidazo[1,2-a]pyridin-7-yl)-amide

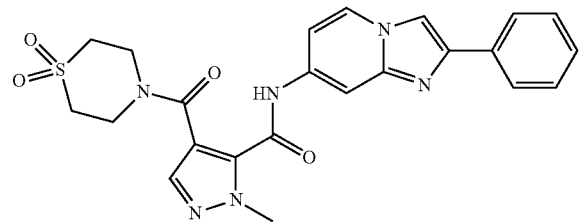

The title compound was prepared in analogy to Example 13, using thiomorpholine 1,1-dioxide in step 2. MS (m/e)=479.2 [M+H$^+$].

Example 49

2-Methyl-4-(3-oxo-piperazine-1-carbonyl)-2H-pyrazole-3-carboxylic acid (2-phenyl-imidazo[1,2-a]pyridin-7-yl)-amide

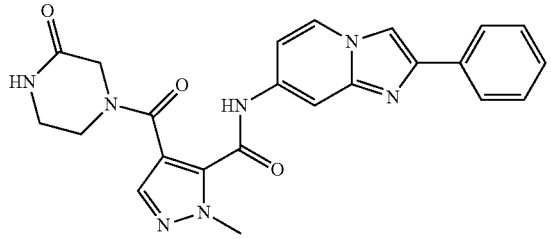

The title compound was prepared in analogy to Example 13, using piperazin-2-one in step 2. MS (m/e)=444.3 [M+H$^+$].

Example 50

4-(3-Hydroxy-azetidine-1-carbonyl)-2-methyl-2H-pyrazole-3-carboxylic acid (2-phenyl-imidazo[1,2-a]pyridin-7-yl)-amide

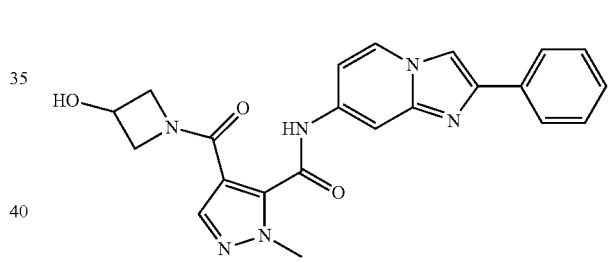

The title compound was prepared in analogy to Example 13, using azetidin-3-ol in step 2. MS (m/e)=417.3 [M+H$^+$].

Example 51

2-Methyl-4-((1S,4S)-2-oxa-5-aza-bicyclo[2.2.1]heptane-5-carbonyl)-2H-pyrazole-3-carboxylic acid (2-phenyl-imidazo[1,2-a]pyridin-7-yl)-amide

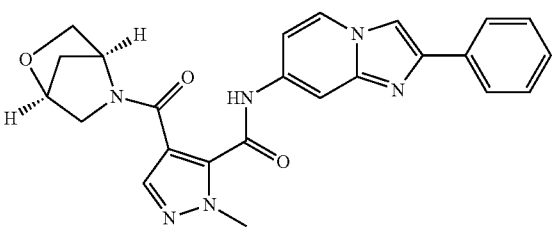

The title compound was prepared in analogy to Example 13, using (1S,4S)-2-oxa-5-aza-bicyclo[2.2.1]heptane in step 2. MS (m/e)=443.3 [M+H$^+$].

Example 52

2-Methyl-4-(4-methyl-piperazine-1-carbonyl)-2H-pyrazole-3-carboxylic acid (2-phenyl-imidazo[1,2-a]pyridin-7-yl)-amide

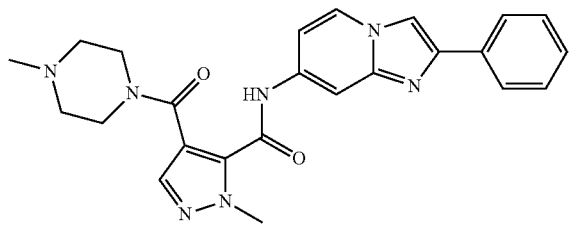

The title compound was prepared in analogy to Example 13, using 1-methyl-piperazine in step 2. MS (m/e)=444.3 [M+H$^+$].

Example 53

4-(3-Hydroxymethyl-morpholine-4-carbonyl)-2-methyl-2H-pyrazole-3-carboxylic acid (2-phenyl-imidazo[1,2-a]pyridin-7-yl)-amide

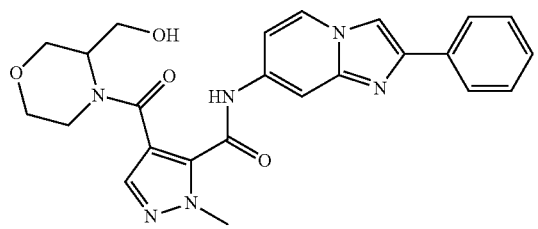

The title compound was prepared in analogy to Example 13, using morpholin-3-yl-methanol in step 2. MS (m/e)=461.2 [M+H$^+$].

Example 54

2-Methyl-2H-pyrazole-3,4-dicarboxylic acid 4-phenylamide 3-[(2-phenyl-imidazo[1,2-a]pyridin-7-yl)-amide]

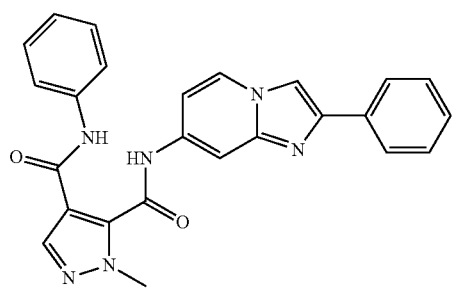

The title compound was prepared in analogy to Example 13, using phenylamine in step 2. MS (m/e)=437.2 [M+H$^+$].

Example 55

2-Methyl-2H-pyrazole-3,4-dicarboxylic acid 3-[(2-phenyl-imidazo[1,2-a]pyridin-7-yl)-amide]-4-pyridin-4-ylamide

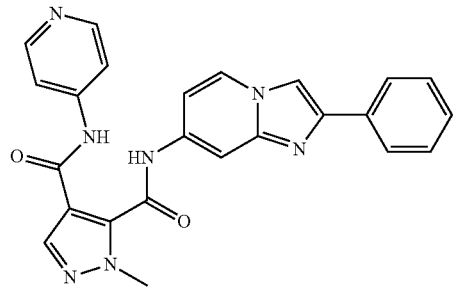

The title compound was prepared in analogy to Example 13, using pyridin-4-ylamine in step 2. MS (m/e)=438.2 [M+H$^+$].

Example 56

2-Methyl-2H-pyrazole-3,4-dicarboxylic acid 4-[bis-(2-hydroxy-ethyl)-amide]3-[(2-phenyl-imidazo[1,2-a]pyridin-7-yl)-amide]

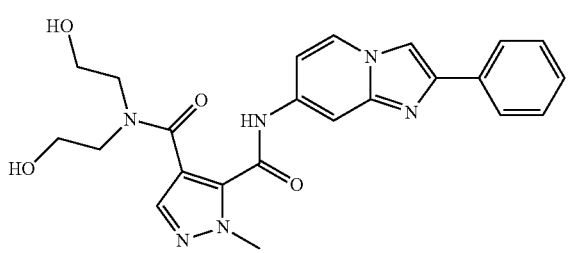

The title compound was prepared in analogy to Example 13, using 2-(2-hydroxy-ethylamino)-ethanol in step 2. MS (m/e)=449.2 [M+H$^+$].

Example 57

2-Methyl-2H-pyrazole-3,4-dicarboxylic acid 4-[(1-hydroxymethyl-propyl)-amide]3-[(2-phenyl-imidazo[1,2-a]pyridin-7-yl)-amide]

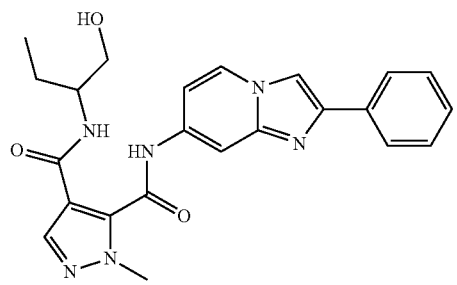

The title compound was prepared in analogy to Example 13, using 2-amino-butan-1-ol in step 2. MS (m/e)=433.2 [M+H$^+$].

Example 58

4-(3-Hydroxy-pyrrolidine-1-carbonyl)-2-methyl-2H-pyrazole-3-carboxylic acid (2-phenyl-imidazo[1,2-a]pyridin-7-yl)-amide

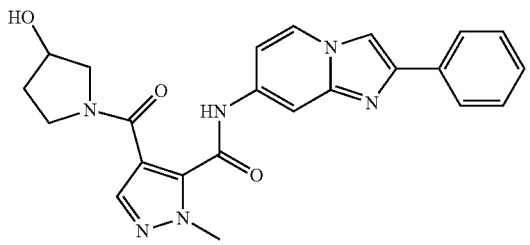

The title compound was prepared in analogy to Example 13, using pyrrolidin-3-ol in step 2. MS (m/e)=431.2 [M+H$^+$].

Example 59

4-(3-Dimethylamino-pyrrolidine-1-carbonyl)-2-methyl-2H-pyrazole-3-carboxylic acid (2-phenyl-imidazo[1,2-a]pyridin-7-yl)-amide

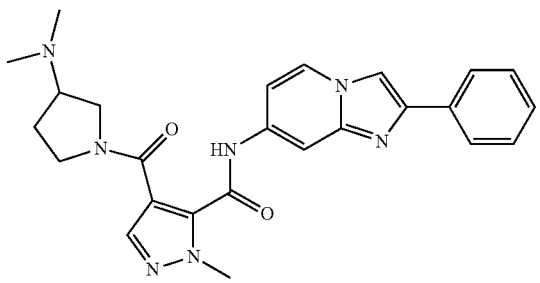

The title compound was prepared in analogy to Example 13, using dimethyl-pyrrolidin-3-yl-amine in step 2. MS (m/e)= 458.3 [M+H$^+$].

Example 60

2-Methyl-2H-pyrazole-3,4-dicarboxylic acid 4-[(2,3-dihydroxy-propyl)-methyl-amide]3-[(2-phenyl-imidazo[1,2-a]pyridin-7-yl)-amide]

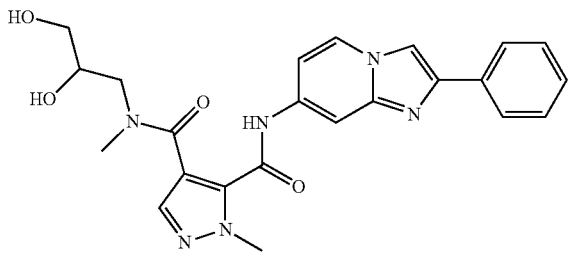

The title compound was prepared in analogy to Example 13, using 3-methylamino-propane-1,2-diol in step 2. MS (m/e)=449.2 [M+H$^+$].

Example 61

2-Methyl-2H-pyrazole-3,4-dicarboxylic acid 4-[(2-methoxy-ethyl)-amide]3-[(2-phenyl-imidazo[1,2-a]pyridin-7-yl)-amide]

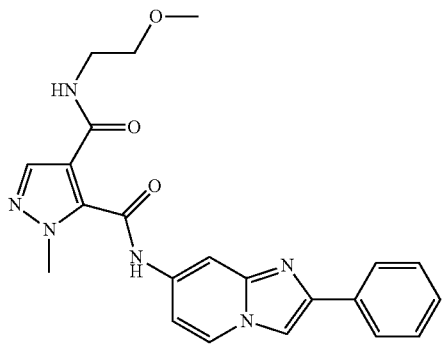

The title compound was prepared in analogy to Example 13, using 2-methoxy-ethylamine in step 2. MS (m/e)=419.2 [M+H$^+$].

Example 62

4-(Azetidine-1-carbonyl)-2-ethyl-2H-pyrazole-3-carboxylic acid (2-phenyl-imidazo[1,2-a]pyridin-7-yl)-amide

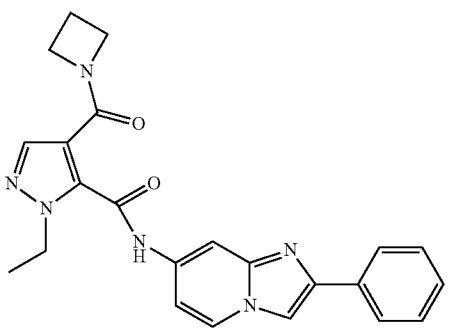

Step 1: 1-Ethyl-5-(2-phenyl-imidazo[1,2-a]pyridin-7-ylcarbamoyl)-1H-pyrazole-4-carboxylic acid KOH (70 mg) was added to a solution of 1-ethyl-5-(2-phenyl-imidazo[1,2-a]pyridin-7-ylcarbamoyl)-1H-pyrazole-4-carboxylic acid ethyl ester (Example 12, 215 mg, 0.53 mmol) in ethanol (6 ml), and the mixture was heated to reflux until HPLC control indicated the consumption of the starting material (2 h). Upon cooling, HCl (conc.) was added dropwise, until the pH reached ~2 (few drops). The suspension was stirred at r.t. (30 min.) and then filtered. The precipitate was washed with little ethanol and dried under vacuum. The thus obtained title compound (160 mg, 80%) was used in the next step without further purification. MS (m/e)=376.4 [M+H$^+$].

Step 2: 4-(Azetidine-1-carbonyl)-2-ethyl-2H-pyrazole-3-carboxylic acid (2-phenyl-imidazo[1,2-a]pyridin-7-yl)-amide TBTU (82 mg) and diisopropylamine (83 mg) were added to a solution of 1-ethyl-5-(2-phenyl-imidazo[1,2-a]pyridin- 7-ylcarbamoyl)-1H-pyrazole-4-carboxylic acid (80 mg, 0.21 mmol) in DMF (1 ml). After stirring this mixture for 30 min (r.t.), azetidine (37 mg, 0.65 mmol) was added to the light brown solution. The mixture was stirred at r.t. overnight, and the title compound (21 mg, 24%) was isolated from the mixture by preparative, inverse-phase HPLC (Agilent Zorbax XdB-C18 column, time per run ~7 min, flow rate 30 ml/min, solvent gradient $H_2O/CH_3CN$=95:5-5:95). MS (m/e)=415.3 [M+H$^+$].

Example 63

4-Chloro-2-methyl-2H-pyrazole-3-carboxylic acid (5-morpholin-4-yl-2-phenyl-imidazo[1,2-c]pyrimidin-7-yl)-amide

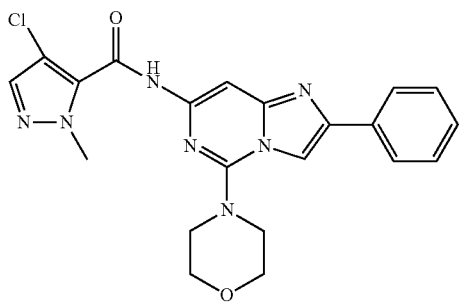

Step 1: 5-Morpholin-4-yl-2-phenyl-imidazo[1,2-c]pyrimidin-7-ylamine

A mixture of 2-morpholin-4-yl-pyrimidine-4,6-diamine (1.0 g, 5.1 mmol), w-bromoacetophenone (1.02 g, 5.1 mmol), NaHCO$_3$ (473 mg, 6 mmol) and methanol (15 ml) was heated under an atmosphere of argon to reflux (3 h). After cooling, water (10 ml) was added (the gummy precipitate could not be isolated). Methanol was evaporated, the residue was taken up in ethyl acetate, washed (water), and dried (Na$_2$SO$_4$). The solvent was evaporated and the title compound (900 mg, 50%) was isolated from the mixture by column chromatography (silica gel, heptane:ethyl acetate=80:20-60:40). MS (m/e)=296.3 [M+H$^+$].

Step 2: 4-Chloro-2-methyl-2H-pyrazole-3-carboxylic acid (5-morpholin-4-yl-2-phenyl-imidazo[1,2-c]pyrimidin-7-yl)-amide Under an atmosphere of nitrogen, N—N-diisopropylethylamine (121 mg) and 2-(1H-benzotriazole-1-yl)-1,1,3,3-tetramethyluronium tetrafluoroborate (TBTU, 120 mg) were added to a solution of 4-chloro-2-methyl-2H-pyrazole-3-carboxylic acid (50 mg, 0.31 mmol, Art-Chem B000148) in DMF (3 ml). After 30 min, 5-morpholin-4-yl-2-phenyl-imidazo[1,2-c]pyrimidin-7-ylamine (110 mg, 0.37 mmol) was added, and the black solution was stirred at r.t. overnight. The reaction mixture was taken up in ethyl acetate and washed with water. After drying (Na$_2$SO$_4$), the solvent was evaporated and the title compound (2 mg, 1.1%) was isolated by preparative, inverse-phase HPLC (Agilent Zorbax XdB-C18 column, time per run ~7 min, flow rate 30 ml/min, solvent gradient $H_2O/CH_3CN$=95:5-5:95). MS (m/e)=438.2 [M+H$^+$].

Example 64

2-Methyl-2H-pyrazole-3,4-dicarboxylic acid 3-{[2-(3-chloro-phenyl)-imidazo[1,2-a]pyridin-7-yl]-amide}4-dimethylamide

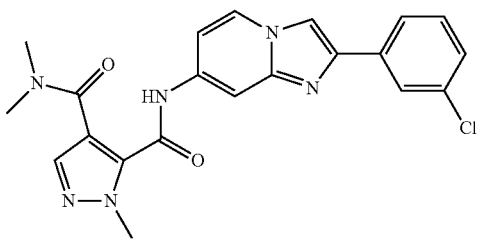

The title compound was prepared in analogy to Example 1, using 3-chlorophenacyl bromide in step 1, and 4-dimethylcarbamoyl-2-methyl-2H-pyrazole-3-carboxylic acid (Art-Chem, B026646) in step 5. MS (m/e)=423.1 [M+H$^+$].

Example 65

2H-Pyrazole-3,4-dicarboxylic acid 4-methylamide 3-[(2-phenyl-imidazo[1,2-a]pyridin-7-yl)-amide]

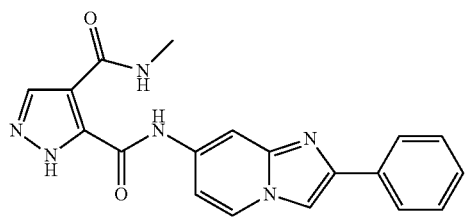

Methylamine (2N in methanol, 2 ml) was added to a solution of 5-(2-phenyl-imidazo[1,2-a]pyridin-7-ylcarbamoyl)-1H-pyrazole-4-carboxylic acid ethyl ester (Example 11, 65 mg, 0.17 mmol) in THF (2 ml), and the mixture was stirred at r.t. (48 h). An additional amount of Methylamine (2N in methanol, 2 ml) was added, and the mixture was stirred at r.t. overnight. The solvent was evaporated and the title compound (20 mg, 32%) was isolated from the residue by preparative, inverse-phase HPLC (Agilent Zorbax XdB-C18 column, time per run ~7 min, flow rate 30 ml/min, solvent gradient $H_2O/CH_3CN$=95:5-5:95). MS (m/e)=361.2 [M+H$^+$].

Example 66

2-Methyl-2H-pyrazole-3,4-dicarboxylic acid 4-[(2-hydroxy-1-hydroxymethyl-ethyl)-amide]3-[(2-phenyl-imidazo[1,2-a]pyridin-7-yl)-amide]

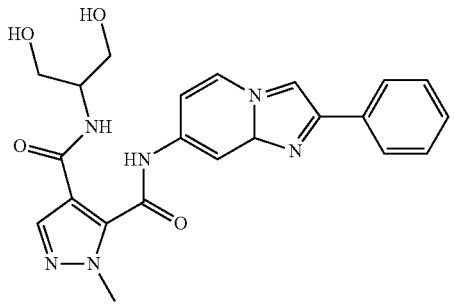

The title compound was prepared in analogy to Example 13, using 2-amino-propane-1,3-diol in step 2. MS (m/e)=435.2 [M+H$^+$].

Example 67

4-(Azetidine-1-carbonyl)-2-methyl-2H-pyrazole-3-carboxylic acid (6-bromo-2-phenyl-imidazo[1,2-a]pyridin-7-yl)-amide

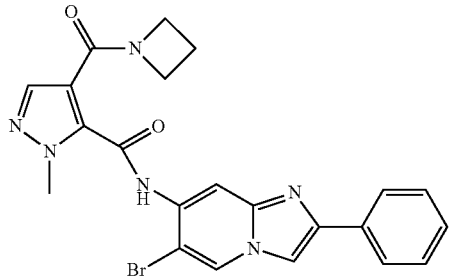

Step 1: 6-Bromo-2-phenyl-imidazo[1,2-a]pyridine-7-carboxylic acid methyl ester

2-Bromoacetophenone (17.29 g, 87 mmol) and NaHCO$_3$ (8.03 g, 96 mmol) were added to a solution of methyl 2-amino-5-bromoisonicotinate (20.07 g, 87 mmol) in methanol (240 ml), and the mixture was heated to reflux (5 h). After cooling to r.t., water (75 ml) was added, and the brown suspension was stirred (15 min) and filtered. The precipitate was washed with a small amount of methanol. The title compound (10.11 g, 35%) was dried under vacuum and was used in the next step without further purification.

Step 2: 6-Bromo-2-phenyl-imidazo[1,2-a]pyridine-7-carboxylic acid

NaOH (1N, 61 ml) was added to a suspension of 6-bromo-2-phenyl-imidazo[1,2-a]pyridine-7-carboxylic acid methyl ester (10.11 g, 31 mmol) in a mixture of water (30 ml) and ethanol (60 ml), and the mixture was heated to reflux (2 h). The mixture was cooled (0° C.) and HCl (conc., ~10 ml) was slowly added. The dark brown suspension was filtered, washed with a small amount of ethanol, and dried under vacuum. The obtained title compound (9.47 g, 98%) was used in the next step without further purification. MS (m/e)=318.9 [M+H$^+$].

Step 3: (6-Bromo-2-phenyl-imidazo[1,2-a]pyridin-7-yl)-carbamic acid tert-butyl ester Under an atmosphere of argon, diphenylphosphoryl azide (8.20 g, 29 mmol) was added to a solution of 6-bromo-2-phenyl-imidazo[1,2-a]pyridine-7-carboxylic acid (9.16 g, 29 mmol) and triethylamine (5.8 g, 58 mmol) in tert-butanol (86 ml). The mixture was heated to reflux overnight, then cooled and diluted with ethyl acetate. The mixture was washed (NH$_4$Cl satd.), and dried (Na$_2$SO$_4$). The title compound (2.75 g, 25%) was isolated from the residue by column chromatography (silica gel, heptane:ethyl acetate=100:0-50:50). MS (m/e)=388.1 [M+H$^+$].

Step 4: 6-Bromo-2-phenyl-imidazo[1,2-a]pyridin-7-ylamine

Trifluoroacetic acid (15 ml) was added to a solution of (6-bromo-2-phenyl-imidazo[1,2-a]pyridin-7-yl)-carbamic acid tert-butyl ester (2.75 g, 7.1 mmol) in CH$_2$Cl$_2$ (15 ml), and the mixture was stirred at r.t. overnight. The mixture was then washed (water, 2×50 ml), dried (Na$_2$SO$_4$), and the solvent was evaporated to give a first crop of the desired product. The water layer was made alkaline by addition of NaOH (conc. 14 ml), and extracted with dichloromethane. The combined organic layers were dried (Na$_2$SO$_4$) and evaporated to give a second crop of the desired product. The combined crops (2.02 g, 99%) were used in the next step without further purification. MS (m/e)=288.0 [M+H$^+$].

Step 5: 5-(6-Bromo-2-phenyl-imidazo[1,2-a]pyridin-7-ylcarbamoyl)-1-methyl-1H-pyrazole-4-carboxylic acid ethyl ester A solution of 5-chlorocarbonyl-1-methyl-1H-pyrazole-4-carboxylic acid ethyl ester (as prepared in Example 14, Step 2, 2.35 g, 10.8 mmol) in dichloromethane (5 ml) was added dropwise over 20 min to a cooled (0° C.) solution of 6-bromo-2-phenyl-imidazo[1,2-a]pyridin-7-ylamine (1.56 g, 5.4 mmol) and triethylamine (877 mg) in dichloromethane (20 ml); the mixture was then stirred for at r.t. (30 min). The mixture was washed (water), and the organic layer was dried (Na$_2$SO$_4$), and evaporated. The title compound (460 mg, 23%) was isolated by filtration over a column of silica gel with dichloromethane as an eluent, and was used without further purification in the next step. MS (m/e)=470.1 [M+H$^+$].

Step 6: 5-(6-Bromo-2-phenyl-imidazo[1,2-a]pyridin-7-ylcarbamoyl)-1-methyl-1H-pyrazole-4-carboxylic acid NaOH (3N, 0.65 ml) was added to a solution of 5-(6-bromo-2-phenyl-imidazo[1,2-a]pyridin-7-ylcarbamoyl)-1-methyl-1H-pyrazole-4-carboxylic acid ethyl ester (460 mg, 0.98 mmol) in a mixture of THF (5 ml) and methanol (5 ml), and the reaction mixture was stirred at r.t. overnight. An additional amount of NaOH (3N, 0.65 ml) and water (2 ml) were added and the mixture was heated to reflux (1 h). After cooling to r.t., HCl (conc., ~0.7 ml) was added to the cooled mixture, and the brown suspension was stirred at r.t. (15 min). The suspension was then filtered, and the precipitated title compound (150 mg, 35%) was washed with a small amount of water, dried under vacuum, and used in the next step without further purification. MS (m/e)=440.3 [M+H$^+$].

Step 7: 4-(Azetidine-1-carbonyl)-2-methyl-2H-pyrazole-3-carboxylic acid (6-bromo-2-phenyl-imidazo[1,2-a]pyridin-7-yl)-amide TBTU (159 mg) and diisopropylethylamine (128 mg) were added to a solution of 5-(6-bromo-2-phenyl-imidazo[1,2-a]pyridin-7-ylcarbamoyl)-1-methyl-1H-pyrazole-4-carboxylic acid (145 mg, 0.33 mmol) in DMF (3 ml), and the light-brown solution was stirred at r.t. (30 min). Azetidine (56 mg, 0.98 mmol) was added and the mixture was stirred at r.t. overnight. The reaction mixture was taken up in ethyl acetate and washed (water). The organic layers were dried (Na$_2$SO$_4$) and evaporated. The title compound (32 mg, 20%) was isolated from the residue by column chromatography (silica gel, heptane:ethyl acetate=50:50-0:100), followed by preparative, inverse-phase HPLC (Agilent Zorbax XdB-C18 column, time per run ~7 min, flow rate 30 ml/min, solvent gradient H$_2$O/CH$_3$CN=95:5-5:95). MS (m/e)=479.1 [M+H$^+$].

Example 68

4-(Azetidine-1-carbonyl)-2-methyl-2H-pyrazole-3-carboxylic acid (6-cyano-2-phenyl-imidazo[1,2-a]pyridin-7-yl)-amide

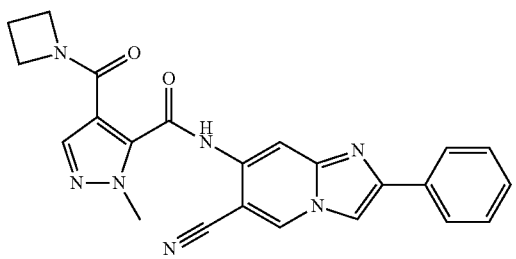

Step 1: 7-Amino-2-phenyl-imidazo[1,2-a]pyridine-6-carbonitrile

2-Bromoacetophenone (1.11 g, 5.6 mmol) and NaHCO$_3$ (470 mg) were added to a solution of 3-cyano-4,6-diaminopyridine (500 mg, 3.7 mmol) in methanol (7.5 ml), and the mixture was heated to reflux overnight. Upon cooling, water (4 ml) was added and the precipitate was filtered and dried under vacuum to give a first crop of the desired product. The filtrate was evaporated, the residue was taken up in ethyl acetate (20 ml) and washed (water, brine). The organic layer was dried (Na$_2$SO$_4$) and evaporated. The residue was purified by column chromatography (silica gel, heptane:ethyl acetate=100:0-50:50) to give a second crop of the desired product. The combined crops gave the title compound (350 mg, 40%). MS (m/e)=235.1 [M+H$^+$].

4-(Azetidine-1-carbonyl)-2-methyl-2H-pyrazole-3-carboxylic acid (6-cyano-2-phenyl-imidazo[1,2-a]pyridin-7-yl)-amide The title compound was prepared in analogy to Example 67, Steps 5-7, using 7-amino-2-phenyl-imidazo[1,2-a]pyridine-6-carbonitrile in Step 5. MS (m/e)=426.1 [M+H$^+$].

Example 69

2-Methyl-4-(morpholine-4-carbonyl)-2H-pyrazole-3-carboxylic acid (6-cyano-2-phenyl-imidazo[1,2-a]pyridin-7-yl)-amide

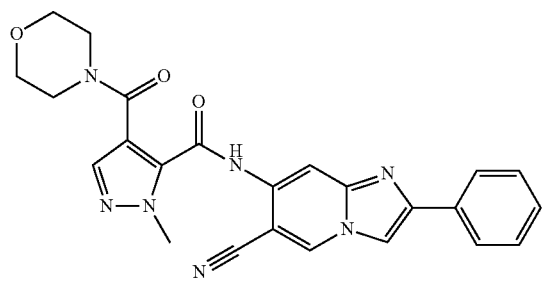

The title compound was prepared in analogy to Example 67, Steps 5-7, using 7-amino-2-phenyl-imidazo[1,2-a]pyridine-6-carbonitrile (as prepared in Example 68, Step 1) in Step 5, and morpholine in Step 7. MS (m/e)=456.2 [M+H$^+$].

Example 70

4-(Azetidine-1-carbonyl)-2-methyl-2H-pyrazole-3-carboxylic acid (6-chloro-2-phenyl-imidazo[1,2-a]pyridin-7-yl)-amide

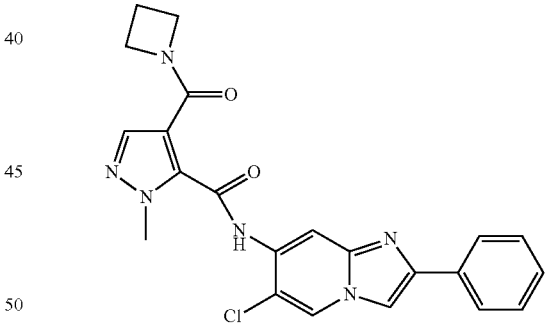

Step 1: 6-Chloro-2-phenyl-imidazo[1,2-a]pyridin-7-ylamine

A mixture of (6-bromo-2-phenyl-imidazo[1,2-a]pyridin-7-yl)-carbamic acid tert-butyl ester (as prepared in Example 67, Step 3, 1.00 g, 2.6 mmol), NiCl$_2$ (668 mg, 5.1 mmol) and NMP (1-methyl-2-pyrolidone, 8 ml) was heated in a sealable tube in a microwave oven to 230° C. (5 min). The reaction mixture was taken up in ethyl acetate and extracted with an aquaeous Na$_2$CO$_3$ solution (2N). The organic layers were dried (Na$_2$SO$_4$) and evaporated. The title compound (240 mg, 38%) was isolated from the residue by column chromatography (silica gel, heptane:ethyl acetate=50:50-0:100). MS (m/e)=244.1 [M+H$^+$].

4-(Azetidine-1-carbonyl)-2-methyl-2H-pyrazole-3-carboxylic acid (6-chloro-2-phenyl-imidazo[1,2-a]pyridin-7-yl)-amide The title compound was prepared in analogy to Example 67, Steps 5-7, using 6-chloro-2-phenyl-imidazo[1,2-a]pyridin-7-ylamine in Step 5. MS (m/e)=435.3 [M+H⁺].

Example 71

4-(Azetidine-1-carbonyl)-2-methyl-2H-pyrazole-3-carboxylic acid (2-phenyl-5-piperidin-1-yl-imidazo[1,2-c]pyrimidin-7-yl)-amide

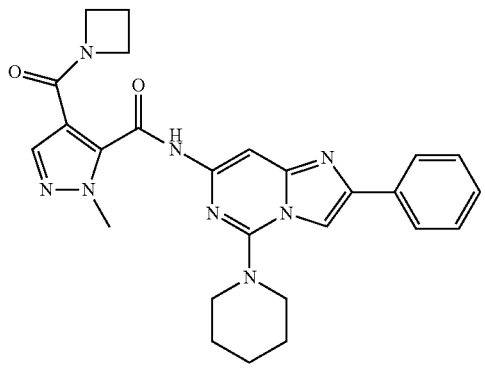

Step 1: 2-Phenyl-5-piperidin-1-yl-imidazo[1,2-c]pyrimidin-7-ylamine

The title compound was prepared in analogy to 5-morpholin-4-yl-2-phenyl-imidazo[1,2-c]pyrimidin-7-ylamine (Example 63, Step 1) from 2-piperidin-1-yl-pyrimidine-4,6-diamine. MS (m/e)=294.2 [M+H⁺].

4-(Azetidine-1-carbonyl)-2-methyl-2H-pyrazole-3-carboxylic acid (2-phenyl-5-piperidin-1-yl-imidazo[1,2-c]pyrimidin-7-yl)-amide The title compound was prepared in analogy to Example 67, Steps 5-7, using 2-phenyl-5-piperidin-1-yl-imidazo[1,2-c]pyrimidin-7-ylamine in Step 5. MS (m/e)=485.2 [M+H⁻].

Example 72

2-Methyl-4-(morpholine-4-carbonyl)-2H-pyrazole-3-carboxylic acid (6-chloro-2-phenyl-imidazo[1,2-a]pyridin-7-yl)-amide

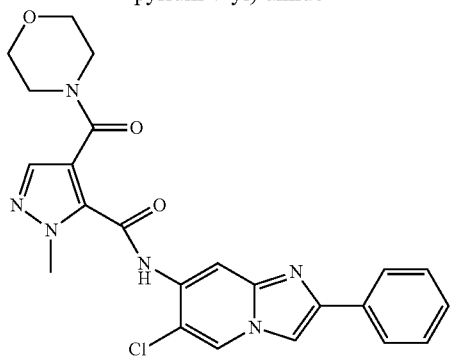

The title compound was prepared in analogy to Example 70, using morpholine in the final step. MS (m/e)=465.3 [M+H⁺].

Example 73

2-Methyl-4-(morpholine-4-carbonyl)-2H-pyrazole-3-carboxylic acid (5-morpholin-4-yl-2-phenyl-imidazo[1,2-c]pyrimidin-7-yl)-amide

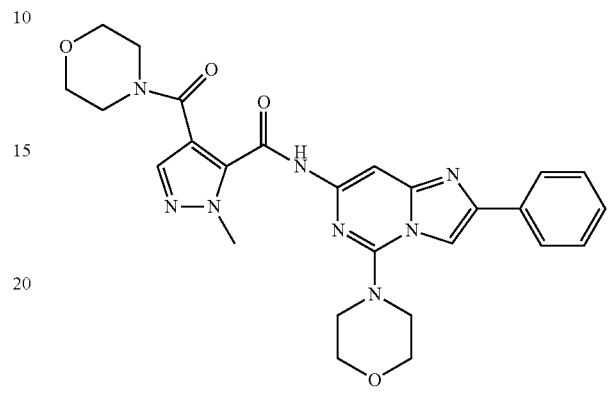

Step 1: 1-Methyl-5-(5-morpholin-4-yl-2-phenyl-imidazo[1,2-c]pyrimidin-7-ylcarbamoyl)-1H-pyrazole-4-carboxylic acid The title compound was prepared in analogy to 5-(6-bromo-2-phenyl-imidazo[1,2-a]pyridin-7-ylcarbamoyl)-1-methyl-1H-pyrazole-4-carboxylic acid (Example 67, Step 4-6), using 5-morpholin-4-yl-2-phenyl-imidazo[1,2-c]pyrimidin-7-ylamine (as prepared in Example 63, Step 1) in Step 4. MS (m/e)=448.3 [M+H⁺].

2-Methyl-4-(morpholine-4-carbonyl)-2H-pyrazole-3-carboxylic acid (5-morpholin-4-yl-2-phenyl-imidazo[1,2-c]pyrimidin-7-yl)-amide The title compound was prepared in analogy to Example 13, Step 2, using morpholine and 1-methyl-5-(5-morpholin-4-yl-2-phenyl-imidazo[1,2-c]pyrimidin-7-ylcarbamoyl)-1H-pyrazole-4-carboxylic acid. MS (m/e)=517.2 [M+H⁺].

Example 74

4-(Azetidine-1-carbonyl)-2-methyl-2H-pyrazole-3-carboxylic acid (6-cyclopropyl-2-phenyl-imidazo[1,2-a]pyridin-7-yl)-amide

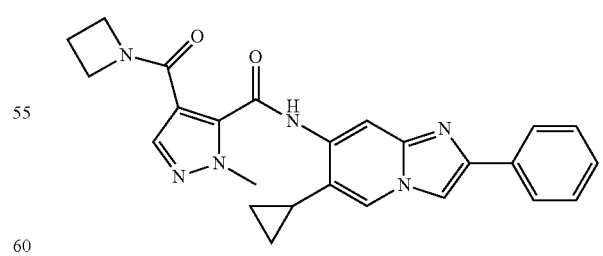

Step 1: 2-Methyl-2H-pyrazole-3,4-dicarboxylic acid 3-ethyl ester

X-Zyme 6134 (20%, 90 mg) was added to a suspension of 2-methyl-2H-pyrazole-3,4-dicarboxylic acid diethyl ester (as prepared in Example 10, Step 1, 4.5 g, 19.5 mmol) in KPI (100 mM, pH 7.2, 450 ml). Sodium hydroxide solution (1 M, total amount 23.2 ml) was added slowly as needed to keep the pH constantly at 7.2 over the course of the reaction. After 18.5 h, the reaction mixture was extracted with tert-butyl methyl ether (TBME) to remove unwanted byproducts. The water layer was then acidified (pH 3.9) by addition of $H_2SO_4$, and extracted several times with TBME. During these extractions, the pH of the water layer was adjusted by addition of $H_2SO_4$ to a pH range between 4.2 and 3.8. After drying ($Na_2SO_4$) and evaporating the combined organic layers, a first crop of title compound (2.90 g, 74%) was obtained as a light grey solid. An additional crop of title compound (0.21 g, 5.3%) was obtained by adding brine to the water layer, repeated extraction with TBME, drying ($Na_2SO_4$) of the combined organic layers, and evaporation.

Step 2: 4-(Azetidine-1-carbonyl)-2-methyl-2H-pyrazole-3-carboxylic acid ethyl ester Propylphosphonic anhydride solution (50% in ethyl acetate, 8.0 ml) was added to a cooled (0° C.) solution of 2-methyl-2H-pyrazole-3,4-dicarboxylic acid 3-ethyl ester (1.00 g, 5.0 mmol), azetidine (576 mg, 10.1 mmol), and N,N-diisopropylethylamine (2.0 g) in ethyl acetate (40 ml). The mixture was stirred for 30 min at 0° C. and overnight at r.t. The reaction mixture was taken up in ethyl acetate, washed with water, dried ($Na_2SO_4$) and evaporated. The obtained title compound (1.32 g, 99%) was used in the next step without further purification. MS (m/e)=238.3 [M+H$^+$].

Step 3: 4-(Azetidine-1-carbonyl)-2-methyl-2H-pyrazole-3-carboxylic acid

NaOH (1N, 10 ml) was added to a solution of 4-(azetidine-1-carbonyl)-2-methyl-2H-pyrazole-3-carboxylic acid ethyl ester (1.32 g, 5.0 mmol) in THF (50 ml), and the mixture was stirred at r.t. (3.5 h). The mixture was neutralized by addition of HCl (1N, 10 ml). The mixture was evaporated under vacuum and the title compound, containing theoretically 2 equiv. of NaCl, (1.72 g, 99%) was used in Step 6 without further purification. MS (m/e)=210.2 [M+H$^+$].

Step 4: (6-Cyclopropyl-2-phenyl-imidazo[1,2-a]pyridin-7-yl)-carbamic acid tert-butyl ester (6-Bromo-2-phenyl-imidazo[1,2-a]pyridin-7-yl)-carbamic acid tert-butyl ester (Example 67, Step 1-3, 600 mg, 1.54 mmol), cyclopropylboronic acid (265 mg, 3.12 mmol), potassium phosphate (1.64 g), tricyclohexylphosphine (95 mg), and palladium(II) acetate (38 mg) were placed in a round-bottom flask, and the flask was filled with an atmosphere of Argon. Toluene (15 ml) and water (1 ml) were added and the mixture was heated to 100° C. overnight. Upon cooling, the reaction mixture was taken up in ethyl acetate and washed. The organic layers were dried ($Na_2SO_4$) and evaporated. The title compound (470 mg, 87%) was isolated from the residue by column chromatography (silica gel, heptane:ethyl acetate=100:0-60:40). MS (m/e)=350.4 [M+H$^+$].

Step 5: 6-Cyclopropyl-2-phenyl-imidazo[1,2-a]pyridin-7-ylamine

Trifluoroacetic acid (1.5 ml) was added to a solution of (6-cyclopropyl-2-phenyl-imidazo[1,2-a]pyridin-7-yl)-carbamic acid tert-butyl ester (470 mg, 1.35 mmol) in dichloromethane (3 ml), and the mixture was stirred at r.t. (1 h). The mixture was then taken up in dichloromethane and washed. The organic layers were dried ($Na_2SO_4$) and evaporated. The title compound (204 mg, 61%) was isolated from the residue by column chromatography (silica gel, dichloromethane:methanol=100:0-90:10). MS (m/e)=250.1 [M+H$^+$].

Step 6: 4-(Azetidine-1-carbonyl)-2-methyl-2H-pyrazole-3-carboxylic acid (6-cyclopropyl-2-phenyl-imidazo[1,2-a]pyridin-7-yl)-amide Propylphosphonic anhydride solution (50% in ethyl acetate, 0.59 ml) was added to a cooled (0° C.) solution of 6-cyclopropyl-2-phenyl-imidazo[1,2-a]pyridin-7-ylamine (100 mg, 0.40 mmol), 4-(azetidine-1-carbonyl)-2-methyl-2H-pyrazole-3-carboxylic acid (Step 3, 167 mg, 0.51 mmol), and N,N-diisopropylethylamine (311 mg) in ethyl acetate (3 ml). The mixture was stirred for 30 min at 0° C. and overnight at r.t. The reaction mixture was taken up in ethyl acetate, washed with water, dried ($Na_2SO_4$) and evaporated. The title compound (31 mg, 18%) was isolated from the residue by preparative, inverse-phase HPLC (Agilent Zorbax XdB-C18 column, time per run ~7 min, flow rate 30 ml/min, solvent gradient $H_2O$/$CH_3CN$=95:5-5:95). MS (m/e)=441.3 [M+H$^+$].

Example 75

2-Methyl-4-(morpholine-4-carbonyl)-2H-pyrazole-3-carboxylic acid (6-cyclopropyl-2-phenyl-imidazo[1,2-a]pyridin-7-yl)-amide

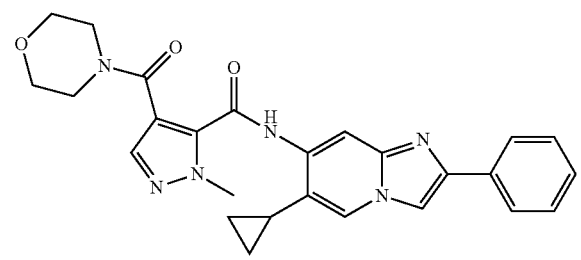

The title compound was prepared in analogy to example 74, using morpholine in Step 2. MS (m/e)=471.4 [M+H$^+$].

Example 76

4-(Azetidine-1-carbonyl)-2-methyl-2H-pyrazole-3-carboxylic acid (5-morpholin-4-yl-2-phenyl-imidazo[1,2-c]pyrimidin-7-yl)-amide

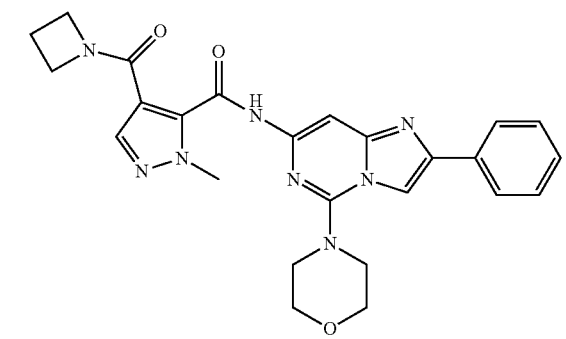

The title compound was prepared in analogy to Example 13, Step 2, using azetidine and 1-methyl-5-(5-morpholin-4- yl-2-phenyl-imidazo[1,2-c]pyrimidin-7-ylcarbamoyl)-1H-pyrazole-4-carboxylic acid (Example 73, Step 1). MS (m/e)=487.2 [M+H⁺].

Example 77

2-Methyl-2H-pyrazole-3,4-dicarboxylic acid 3-[(6-cyano-2-phenyl-imidazo[1,2-a]pyridin-7-yl)-amide]-4-[(3-hydroxy-propyl)-amide]

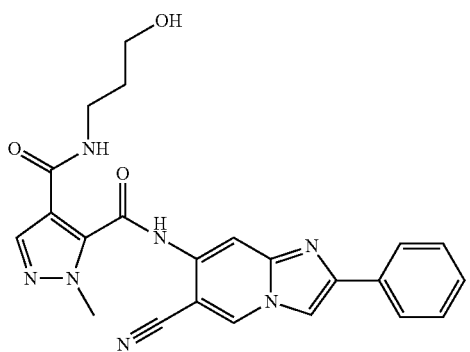

The title compound was prepared in analogy to Example 67, Steps 5-7, using 7-amino-2-phenyl-imidazo[1,2-a]pyridine-6-carbonitrile (as prepared in Example 68, Step 1) in Step 5, and 3-amino-propan-1-ol in Step 7. MS (m/e)=444.4 [M+H⁺].

Example 78

2-Methyl-4-(piperazine-1-carbonyl)-2H-pyrazole-3-carboxylic acid (6-cyano-2-phenyl-imidazo[1,2-a]pyridin-7-yl)-amide

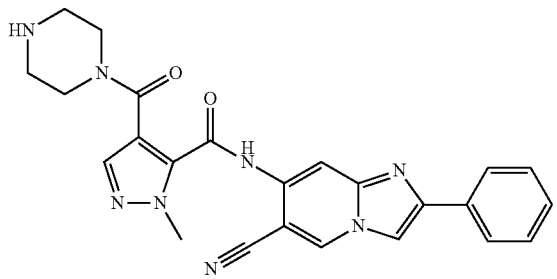

The title compound was prepared in analogy to Example 67, Steps 5-7, using 7-amino-2-phenyl-imidazo[1,2-a]pyridine-6-carbonitrile (as prepared in Example 68, Step 1) in Step 5, and piperazine in Step 7. MS (m/e)=455.3 [M+H⁺].

Example 79

2-Methyl-2H-pyrazole-3,4-dicarboxylic acid 3-[(6-cyano-2-phenyl-imidazo[1,2-a]pyridin-7-yl)-amide]-4-[(2-hydroxy-propyl)-amide]

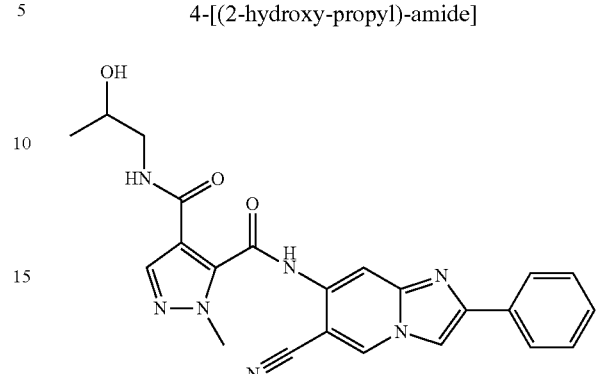

The title compound was prepared in analogy to Example 67, Steps 5-7, using 7-amino-2-phenyl-imidazo[1,2-a]pyridine-6-carbonitrile (as prepared in Example 68, Step 1) in Step 5, and 1-amino-propan-2-ol in Step 7. MS (m/e)=444.4 [M+H⁺].

Example 80

4-Chloro-2-methyl-2H-pyrazole-3-carboxylic acid (2-phenyl-imidazo[1,2-c]pyrimidin-7-yl)-amide

Step 1: 2-Phenyl-imidazo[1,2-c]pyrimidin-7-ylamine

ω-Bromoacetophenone (9.04 g, 45 mmol) and NaHCO₃ (4.30 g, 50 mmol) were added to a solution of 4,6-diaminopyrimidine (5.00 g, 0.45 mmol) in methanol (80 ml), and the mixture was heated to reflux (3 h). Upon cooling, water (40 ml) was added, and the suspension was stirred at r.t. (15 min). The precipitated title compound (5.62 g, 59%) was isolated by filtration, washed with small amounts of water and methanol, and dried under vacuum. MS (m/e)=211.1 [M+H⁺].

Step 2: 4-Chloro-2-methyl-2H-pyrazole-3-carboxylic acid (2-phenyl-imidazo[1,2-c]pyrimidin-7-yl)-amide DMF (8 ml) and diisopropylethylamine (738 mg) were added to 4-chloro-2-methyl-2H-pyrazole-3-carboxylic acid (916 mg, 5.7 mmol) and TBTU (1.83 g), and the mixture was stirred at r.t. (10 min). 2-Phenyl-imidazo[1,2-c]pyrimidin-7-ylamine (400 mg, 1.9 mmol) was added and the mixture was stirred at r.t. overnight. The reaction mixture was then poured on water (35 ml), and the mixture was extracted with ethyl acetate. The combined organic layers were dried (Na₂SO₄) and evaporated. The title compound (45 mg, 6.7%) was isolated from the residue by column chromatography (silica gel, heptane:ethyl acetate=100:0-60:40), followed by preparative, inverse-phase HPLC (Agilent Zorbax XdB-C18 column, time per run ~7 min, flow rate 30 ml/min, solvent gradient H₂O/CH₃CN=95:5-5:95). MS (m/e)=353.1 [M+H⁺].

Example 81

2-Methyl-2H-pyrazole-3,4-dicarboxylic acid 4-amide 3-[(2-phenyl-imidazo[1,2-c]pyrimidin-7-yl)-amide]

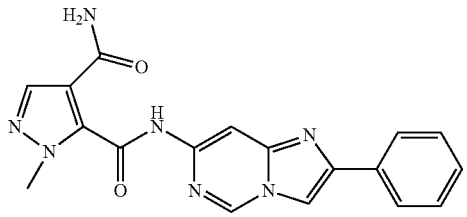

The title compound was prepared in analogy to Example 80, using 4-carbamoyl-2-methyl-2H-pyrazole-3-carboxylic acid in Step 2. MS (m/e)=362.2 [M+H⁺].

Example 82

2-Methyl-2H-pyrazole-3,4-dicarboxylic acid 4-dimethylamide 3-[(2-phenyl-imidazo[1,2-c]pyrimidin-7-yl)-amide]

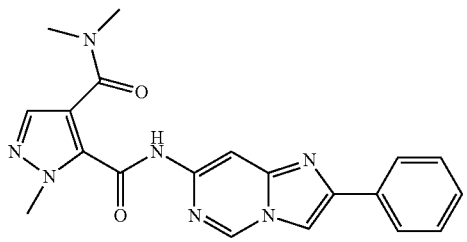

The title compound was prepared in analogy to Example 80, using 4-dimethylcarbamoyl-2-methyl-2H-pyrazole-3-carboxylic acid in Step 2. MS (m/e)=390.3 [M+H⁺].

Example 83

1-Methyl-5-(2-phenyl-imidazo[1,2-c]pyrimidin-7-ylcarbamoyl)-1H-pyrazole-4-carboxylic acid ethyl ester

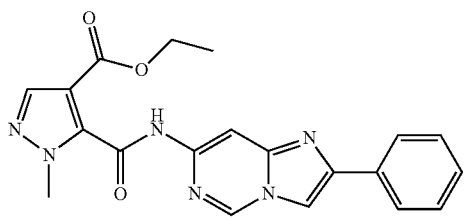

The title compound was prepared in analogy to Example 80, using 2-methyl-2H-pyrazole-3,4-dicarboxylic acid 4-ethyl ester (Example 10, Step 1-2) in Step 2. MS (m/e)= 391.2 [M+H⁺].

Example 84

2-Methyl-2H-pyrazole-3,4-dicarboxylic acid 4-methylamide 3-[(2-phenyl-imidazo[1,2-c]pyrimidin-7-yl)-amide]

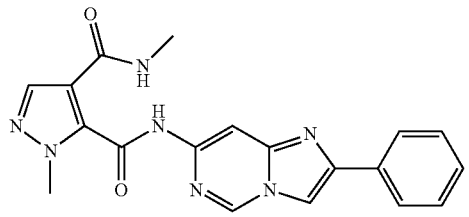

Methylamine (2N in methanol, 4 ml) was added to a solution of 1-methyl-5-(2-phenyl-imidazo[1,2-c]pyrimidin-7-yl-carbamoyl)-1H-pyrazole-4-carboxylic acid ethyl ester (180 mg, 0.46 mmol) in THF (4 ml). The light brown suspension was stirred over the weekend, the solvent was evaporated and the title compound (15 mg, 8.7%) was isolated from the residue by column chromatography (silica gel, heptane:ethyl acetate=60:40-0:100) followed by preparative, inverse-phase HPLC (Agilent Zorbax XdB-C18 column, time per run ~7 min, flow rate 30 ml/min, solvent gradient H₂O/CH₃CN=95:5-5:95). MS (m/e)=376.2 [M+H⁺].

Example 85

2-Methyl-2H-pyrazole-3,4-dicarboxylic acid 4-[(3-methoxy-propyl)-amide]3-[(2-phenyl-imidazo[1,2-c]pyrimidin-7-yl)-amide]

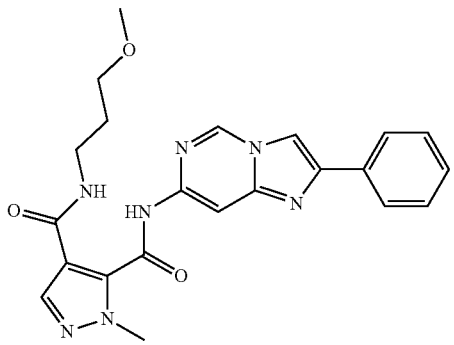

Step 1: 1-Methyl-5-(2-phenyl-imidazo[1,2-c]pyrimidin-7-ylcarbamoyl)-1H-pyrazole-4-carboxylic acid KOH (15 ml of a solution of 0.26 g in 25 ml ethanol) was added to 1-Methyl-5-(2-phenyl-imidazo[1,2-c]pyrimidin-7-ylcarbamoyl)-1H-pyrazole-4-carboxylic acid ethyl ester (Example 83), and the mixture was heated to reflux overnight. The mixture was cooled to r.t. and acidified with HCl (25%, 0.7 ml). The precipitate was filtered, washed with a small amount of ethanol, and dried under vacuum. The obtained title compound was used without further purification in the next step. MS (m/e)=363.2 [M+H⁺].

Step 2: 2-Methyl-2H-pyrazole-3,4-dicarboxylic acid 4-[(3-methoxy-propyl)-amide]3-[(2-phenyl-imidazo[1,2-c]pyrimidin-7-yl)-amide]

In a sealable tube, 3-methoxy-propylamine (21 mg, 0.236 mmol) was added to a mixture of 1-methyl-5-(2-phenyl-imidazo[1,2-c]pyrimidin-7-ylcarbamoyl)-1H-pyrazole-4-carboxylic acid (70 mg, 0.193 mmol), TBTU (74 mg, 0.231 mmol), diisopropylamine (75 mg, 0.581 mmol) and DMF (2 ml), and the mixture was shaken at r.t. overnight. The title compound was obtained from the reaction mixture by preparative, inverse-phase HPLC (Agilent Zorbax XdB-C18 column, time per run ~7 min, flow rate 30 ml/min, solvent gradient $H_2O/CH_3CN$=95:5-5:95). MS (m/e)=434.2 [M+H$^+$].

Example 86

4-(Azetidine-1-carbonyl)-2-methyl-2H-pyrazole-3-carboxylic acid (2-phenyl-imidazo[1,2-c]pyrimidin-7-yl)-amide

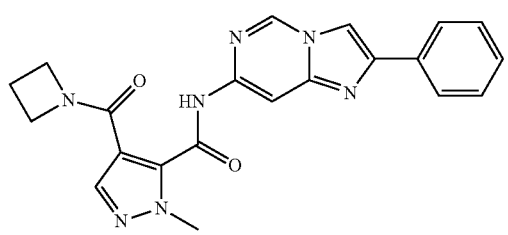

The title compound was prepared in analogy to Example 85, using azetidine in Step 2. MS (m/e)=402.3 [M+H$^+$].

Example 87

2-Methyl-2H-pyrazole-3,4-dicarboxylic acid 4-isopropylamide 3-[(2-phenyl-imidazo[1,2-c]pyrimidin-7-yl)-amide]

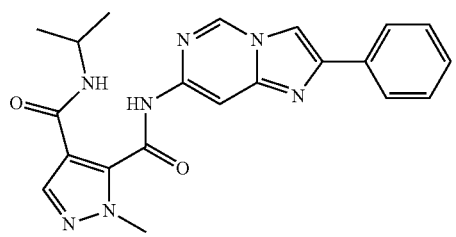

The title compound was prepared in analogy to Example 85, using isopropylamine in Step 2. MS (m/e)=404.3 [M+H$^+$].

Example 88

2-Methyl-2H-pyrazole-3,4-dicarboxylic acid 4-[(2-hydroxy-ethyl)-amide]3-[(2-phenyl-imidazo[1,2-c]pyrimidin-7-yl)-amide]

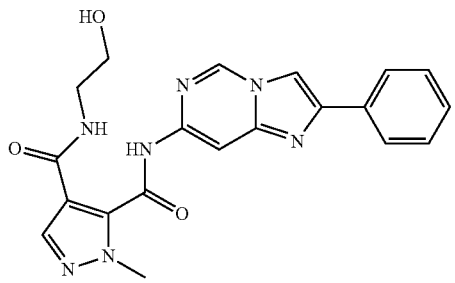

The title compound was prepared in analogy to Example 85, using 2-amino-ethanol in Step 2. MS (m/e)=406.3 [M+H$^+$].

Example 89

2-Methyl-4-(morpholine-4-carbonyl)-2H-pyrazole-3-carboxylic acid (2-phenyl-imidazo[1,2-c]pyrimidin-7-yl)-amide

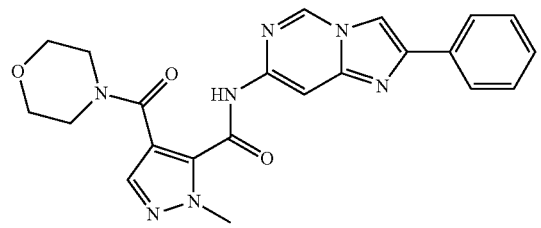

The title compound was prepared in analogy to Example 85, using morpholine in Step 2. MS (m/e)=432.3 [M+H$^+$].

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I)

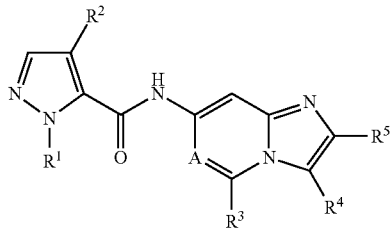

wherein
A is N;
R$^1$ is hydrogen, lower-alkyl or fluoro-lower-alkyl;
R$^2$ is halogen, C(O)NR$^7$R$^8$ or C(O)OR$^9$;
R$^3$ is hydrogen, NR$^{10}$R$^{11}$, lower-alkyl, lower-alkoxy, fluoro-lower-alkyl or fluoro-lower-alkoxy;
R$^4$ is hydrogen, lower-alkyl, fluoro-lower-alkyl, lower alkoxy or fluoro-lower-alkoxy;
R$^5$ is aryl or heteroaryl, each of which is optionally substituted by 1 to 3 substituents independently selected from the group consisting of halogen, lower-alkyl, lower-alkoxy, fluoro-lower-alkyl, fluoro-lower-alkoxy and hydroxy;
R$^7$ and R$^8$ are each independently selected from the group consisting of hydrogen, lower-alkyl, lower-alkoxy-lower-alkyl, fluoro-lower-alkyl, cycloalkyl, cycloalkyl-lower-alkyl, NH$_2$-lower-alkyl, N(H,lower-alkyl)-lower-alkyl, N(lower-alkyl$_2$)-lower-alkyl, hydroxy-lower-alkyl, hydroxy-lower-alkoxy-lower-alkyl, NH$_2$C(O)-lower-alkyl, N(H,lower-alkyl)C(O)-lower-alkyl, N(lower-alkyl$_2$)C(O)-lower-alkyl, lower-alkoxy, hydroxy-lower-alkyl-oxetanyl-lower-alkyl, oxo-tetrahydrofuranyl, tetrahydrofuranyl-lower-alkyl, oxo-tetrahydrofuranyl-lower-alkyl, hydroxy-fluoro-lower-alkyl, tetrahydrofuranyl, aryl and heteroaryl, wherein each aryl or heteroaryl is optionally substituted by 1 to 3 substituents independently selected from the group consisting of halogen, lower-alkyl, lower-alkoxy, fluoro-lower-alkyl, fluoro-lower-alkoxy and hydroxy,
or R$^7$ and R$^8$, together with the nitrogen atom to which they are attached, form a heterocyclyl selected from the group consisting of pyrrolidinyl, azetidinyl, morpholinyl, 5,6-dihydro-8-H-[1,2,4]triazolo[4,3-a]pyrazinyl, 3,4-dihydro-1H-pyrrolo[1,2-a]pyrazinyl, 2-oxa-6-aza-spiro[3.3]heptyl, 5,6-dihydro-8H-imidazo[1,2-a]pyrazinyl, [1,4]oxazepanyl, piperazinyl, thiomorpholinyl and 2-oxa-5-aza-bicyclo[2.2.1]heptyl, which heterocyclyl is optionally substituted by 1 to 3 substituents independently selected from the group consisting of halogen, lower-alkyl, lower-alkyl-C(O), lower-alkoxy-lower-alkyl, oxo, hydroxy, hydroxy-lower-alkyl, N(lower-alkyl$_2$), NH$_2$, N(H,lower-alkyl), fluoro-lower-alkyl, fluoro-lower-alkyl-C(O), lower-alkoxy and fluoro-lower-alkoxy;
R$^9$ is hydrogen, lower-alkyl, or fluoro-lower-alkyl;
R$^{10}$ and R$^{11}$ are each independently hydrogen, lower-alkyl or fluoro-lower-alkyl,
or R$^{10}$ and R$^{11}$, together with the nitrogen atom to which they are attached, form a heterocyclyl selected from the group consisting of piperidinyl, morpholinyl, pyrrolidinyl, azetidinyl and piperazinyl, which heterocyclyl is optionally substituted by 1 to 3 substituents independently selected from the group consisting of halogen, lower-alkyl, lower-alkoxy, fluoro-lower-alkyl and fluoro-lower-alkoxy;

or a pharmaceutically acceptable salt or ester thereof.

2. The compound of claim 1, wherein R$^1$ is hydrogen or lower alkyl.

3. The compound of claim 2, wherein R$^1$ is methyl.

4. The compound of claim 1, wherein R$^2$ is C(O)NR$^7$R$^8$.

5. The compound of claim 1, wherein R$^3$ is hydrogen or NR$^{10}$R$^{11}$.

6. The compound of claim 5, wherein R$^3$ is hydrogen.

7. The compound of claim 1, wherein R$^4$ is hydrogen or lower-alkyl.

8. The compound of claim 7, wherein R$^4$ is hydrogen.

9. The compound of claim 1, wherein R$^5$ is phenyl or thiazolyl, each of which is optionally substituted by 1 to 2 substituents independently selected from halogen.

10. The compound of claim 9, wherein R$^5$ is phenyl.

11. The compound of claim 1, wherein R$^7$ and R$^8$ are each independently selected from the group consisting of hydrogen, lower-alkyl, lower-alkoxy-lower-alkyl, fluoro-lower-alkyl, cycloalkyl, N(H,lower-alkyl)-lower-alkyl, hydroxy-lower-alkyl, hydroxy-lower-alkoxy-lower-alkyl, N(lower-alkyl$_2$)C(O)-lower-alkyl, lower-alkoxy, 3-(hydroxy-lower-alkyl)-oxetan-3-yl-lower-alkyl, 2-oxo-tetrahydrofuranyl, tetrahydrofuranyl-lower-alkyl, hydroxy-fluoro-lower-alkyl, tetrahydrofuranyl, phenyl and pyridinyl,
or R$^7$ and R$^8$, together with the nitrogen atom to which they are attached, form a heterocyclyl selected from the group consisting of pyrrolidinyl, azetidinyl, morpholinyl, 5,6-dihydro-8-H-[1,2,4]triazolo[4,3-a]pyrazinyl, 3,4-dihydro-1H-pyrrolo[1,2-a]pyrazinyl, 2-oxa-6-aza-spiro[3.3]heptyl, 5,6-dihydro-8H-imidazo[1,2-a]pyrazinyl, [1,4]oxazepanyl, piperazinyl, thiomorpholinyl and 2-oxa-5-aza-bicyclo[2.2.1]heptyl, which heterocyclyl is optionally substituted by 1 to 3 substituents independently selected from the group consisting of halogen, lower-alkyl, lower-alkyl-C(O), lower-alkoxy-lower-alkyl, oxo, hydroxy, hydroxy-lower-alkyl, N(lower-alkyl$_2$).

12. The compound of claim 11, wherein R$^7$ and R$^8$ are each independently selected from the group consisting of hydrogen, lower-alkyl, lower-alkoxy-lower-alkyl and hydroxy-lower-alkyl, or R$^7$ and R$^8$, together with the nitrogen atom to which they are attached, form a heterocyclyl selected from the group consisting of azetidinyl and morpholinyl, which heterocyclyl is optionally substituted by 1 to 2 substituents independently selected from the group consisting of halogen and hydroxy.

13. The compound of claim 12, wherein R$^7$ and R$^8$ are each independently selected from the group consisting of hydrogen, methyl, 3-methoxy-propyl and 3-hydroxy-propyl, or R$^7$ and R$^8$, together with the nitrogen atom to which they are attached, form 3,3-difluoro-azetidin-1-yl, morpholin-4-yl, azetidin-1-yl or 3-hydroxy-azetidin-1-yl.

14. The compound of claim 1, wherein R$^9$ is lower-alkyl.

15. The compound of claim 1, wherein $R^{10}$ and $R^{11}$, together with the nitrogen atom to which they are attached, form piperidinyl or morpholinyl.

16. The compound of claim 1, selected from the group consisting of

4-Chloro-2-methyl-2H-pyrazole-3-carboxylic acid (5-morpholin-4-yl-2-phenyl-imidazo[1,2-c]pyrimidin-7-yl)-amide, 4-(Azetidine-1-carbonyl)-2-methyl-2H-pyrazole-3-carboxylic acid (2-phenyl-5-piperidin-1-yl-imidazo[1,2-c]pyrimidin-7-yl)-amide, 2-Methyl-4-(morpholine-4-carbonyl)-2H-pyrazole-3-carboxylic acid (5-morpholin-4-yl-2-phenyl-imidazo[1,2-c]pyrimidin-7-yl)-amide, 4-(Azetidine-1-carbonyl)-2-methyl-2H-pyrazole-3-carboxylic acid (5-morpholin-4-yl-2-phenyl-imidazo[1,2-c]pyrimidin-7-yl)-amide, 4-Chloro-2-methyl-2H-pyrazole-3-carboxylic acid (2-phenyl-imidazo[1,2-c]pyrimidin-7-yl)-amide 2-Methyl-2H-pyrazole-3,4-dicarboxylic acid 4-amide 3-[(2-phenyl-imidazo[1,2-c]pyrimidin-7-yl)-amide], 2-Methyl-2H-pyrazole-3,4-dicarboxylic acid 4-dimethylamide 3-[(2-phenyl-imidazo[1,2-c]pyrimidin-7-yl)-amide], 1-Methyl-5-(2-phenyl-imidazo[1,2-c]pyrimidin-7-ylcarbamoyl)-1H-pyrazole-4-carboxylic acid ethyl ester, 2-Methyl-2H-pyrazole-3,4-dicarboxylic acid 4-methylamide 3-[(2-phenyl-imidazo[1,2-c]pyrimidin-7-yl)-amide], 2-Methyl-2H-pyrazole-3,4-dicarboxylic acid 4-[(3-methoxy-propyl)-amide]3-[(2-phenyl-imidazo[1,2-c]pyrimidin-7-yl)-amide], 4-(Azetidine-1-carbonyl)-2-methyl-2H-pyrazole-3-carboxylic acid (2-phenyl-imidazo[1,2-c]pyrimidin-7-yl)-amide, 2-Methyl-2H-pyrazole-3,4-dicarboxylic acid 4-isopropylamide 3-[(2-phenyl-imidazo[1,2-c]pyrimidin-7-yl)-amide], 2-Methyl-2H-pyrazole-3,4-dicarboxylic acid 4-[(2-hydroxy-ethyl)-amide]3-[(2-phenyl-imidazo[1,2-c]pyrimidin-7-yl)-amide], and 2-Methyl-4-(morpholine-4-carbonyl)-2H-pyrazole-3-carboxylic acid (2-phenyl-imidazo[1,2-c]pyrimidin-7-yl)-amide or a pharmaceutically acceptable salt or ester thereof.

17. The compound of claim 16, selected from the group consisting of

2-Methyl-2H-pyrazole-3,4-dicarboxylic acid 4-dimethylamide 3-[(2-phenyl-imidazo[1,2-c]pyrimidin-7-yl)-amide], 2-Methyl-2H-pyrazole-3,4-dicarboxylic acid 4-[(3-methoxy-propyl)-amide]3-[(2-phenyl-imidazo[1,2-c]pyrimidin-7-yl)-amide], 4-(Azetidine-1-carbonyl)-2-methyl-2H-pyrazole-3-carboxylic acid (2-phenyl-imidazo[1,2-c]pyrimidin-7-yl)-amide, and 2-Methyl-4-(morpholine-4-carbonyl)-2H-pyrazole-3-carboxylic acid (2-phenyl-imidazo[1,2-c]pyrimidin-7-yl)-amide or a pharmaceutically acceptable salt or ester thereof.

18. A pharmaceutical composition comprising a therapeutically effective amount of a compound of formula I

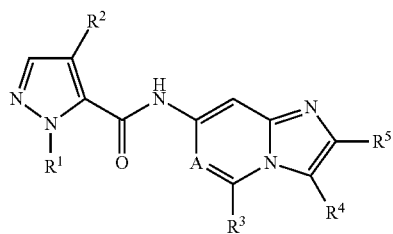

(I)

wherein

A is N;

$R^1$ is hydrogen, lower-alkyl or fluoro-lower-alkyl;

$R^2$ is halogen, C(O)NR$^7$R$^8$ or C(O)OR$^9$;

$R^3$ is hydrogen, NR$^{10}$R$^{11}$, lower-alkyl, lower-alkoxy, fluoro-lower-alkyl or fluoro-lower-alkoxy;

$R^4$ is hydrogen, lower-alkyl, fluoro-lower-alkyl, lower alkoxy or fluoro-lower-alkoxy;

$R^5$ is aryl or heteroaryl, each of which is optionally substituted by 1 to 3 substituents independently selected from the group consisting of halogen, lower-alkyl, lower-alkoxy, fluoro-lower-alkyl, fluoro-lower-alkoxy and hydroxy;

$R^7$ and $R^8$ are each independently selected from the group consisting of hydrogen, lower-alkyl, lower-alkoxy-lower-alkyl, fluoro-lower-alkyl, cycloalkyl, cycloalkyl-lower-alkyl, NH$_2$-lower-alkyl, N(H,lower-alkyl)-lower-alkyl, N(lower-alkyl$_2$)-lower-alkyl, hydroxy-lower-alkyl, hydroxy-lower-alkoxy-lower-alkyl, NH$_2$C(O)-lower-alkyl, N(H,lower-alkyl)C(O)-lower-alkyl, N(lower-alkyl$_2$)C(O)-lower-alkyl, lower-alkoxy, hydroxy-lower-alkyl-oxetanyl-lower-alkyl, oxo-tetrahydrofuranyl, tetrahydrofuranyl-lower-alkyl, oxo-tetrahydrofuranyl-lower-alkyl, hydroxy-fluoro-lower-alkyl, tetrahydrofuranyl, aryl and heteroaryl, wherein each aryl or heteroaryl is optionally substituted by 1 to 3 substituents independently selected from the group consisting of halogen, lower-alkyl, lower-alkoxy, fluoro-lower-alkyl, fluoro-lower-alkoxy and hydroxy, or $R^7$ and $R^8$, together with the nitrogen atom to which they are attached, form a heterocyclyl selected from the group consisting of pyrrolidinyl, azetidinyl, morpholinyl, 5,6-dihydro-8-H-[1,2,4]triazolo[4,3-a]pyrazinyl, 3,4-dihydro-1H-pyrrolo[1,2-a]pyrazinyl, 2-oxa-6-aza-spiro[3.3]heptyl, 5,6-dihydro-8H-imidazo[1,2-a]pyrazinyl, [1,4]oxazepanyl, piperazinyl, thiomorpholinyl and 2-oxa-5-aza-bicyclo[2.2.1]heptyl, which heterocyclyl is optionally substituted by 1 to 3 substituents independently selected from the group consisting of halogen, lower-alkyl, lower-alkyl-C(O), lower-alkoxy-lower-alkyl, oxo, hydroxy, hydroxy-lower-alkyl, N(lower-alkyl$_2$), NH$_2$, N(H,lower-alkyl), fluoro-lower-alkyl, fluoro-lower-alkyl-C(O), lower-alkoxy and fluoro-lower-alkoxy;

$R^9$ is hydrogen, lower-alkyl, or fluoro-lower-alkyl;

$R^{10}$ and $R^{11}$ are each independently hydrogen, lower-alkyl or fluoro-lower-alkyl, or $R^{10}$ and $R^{11}$, together with the nitrogen atom to which they are attached, form a heterocyclyl selected from the group consisting of piperidinyl, morpholinyl, pyrrolidinyl, azetidinyl and piperazinyl, which heterocyclyl is optionally substituted by 1 to 3 substituents independently selected from the group consisting of halogen, lower-alkyl, lower-alkoxy, fluoro-lower-alkyl and fluoro-lower-alkoxy;

or a pharmaceutically acceptable salt or ester thereof and a pharmaceutically acceptable carrier.

* * * * *